United States Patent
Jeys et al.

(10) Patent No.: US 10,228,284 B2
(45) Date of Patent: Mar. 12, 2019

(54) DEVICES AND METHODS FOR SENSING TARGETS USING PHOTOTHERMAL SPECKLE DETECTION

(71) Applicant: Massachusetts Institute of Technology, Cambridge, MA (US)

(72) Inventors: Thomas H. Jeys, Lexington, MA (US); William D. Herzog, Bedford, MA (US); Brian G. Saar, Cambridge, MA (US); Alexander M. Stolyarov, Belmont, MA (US); Ryan Sullenberger, Lexington, MA (US); David Crompton, Lowell, MA (US); Shawn Michael Redmond, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 23 days.

(21) Appl. No.: 15/186,682

(22) Filed: Jun. 20, 2016

(65) Prior Publication Data
US 2017/0211977 A1    Jul. 27, 2017

Related U.S. Application Data

(60) Provisional application No. 62/207,720, filed on Aug. 20, 2015.

(51) Int. Cl.
G01J 5/02    (2006.01)
G01J 3/433   (2006.01)
(Continued)

(52) U.S. Cl.
CPC .............. *G01J 3/433* (2013.01); *G01J 3/108* (2013.01); *G01J 3/2823* (2013.01); *G01J 3/447* (2013.01);
(Continued)

(58) Field of Classification Search
CPC ......... G01N 21/49; B01F 1/00; B01F 5/0618; B01F 5/0646; B01F 5/0655
See application file for complete search history.

(56) References Cited

U.S. PATENT DOCUMENTS

| 4,339,954 A | 7/1982 | Anson et al. |
| 4,489,239 A | 12/1984 | Grant et al. |

(Continued)

FOREIGN PATENT DOCUMENTS

| JP | 2004-101189 A | 4/2004 |
| JP | 2013-92497 A | 5/2013 |

(Continued)

OTHER PUBLICATIONS

Ameri, S., et al., "Photo-displacement imaging," *Electron. Lett.* 17:337-338 (1981).

(Continued)

*Primary Examiner* — David Porta
*Assistant Examiner* — Mamadou Faye
(74) *Attorney, Agent, or Firm* — Hamilton, Brook, Smith & Reynolds, P.C.

(57) ABSTRACT

A device, and corresponding method, can include a pump light source configured to be modulated at a pump modulation and to irradiate a target specimen. The device can also include a probe light source arranged to generate a speckle pattern from the target specimen, as well as a sensor configured to detect changes in at least one of position and intensity of one or more speckle lobes of the speckle pattern having correlation with the pump modulation. The device and method can be used for non-contact monitoring and remote sensing of surfaces, gases, liquids, particles, and other target materials by analyzing speckle pattern changes as a function of pump light irradiation. Advantages can include much higher sensitivity than existing methods; the (Continued)

ability to use visible probe wavelengths for uncooled, low-cost visible detectors with high spatial resolution; and the ability to obtain target material properties without detecting infrared light.

37 Claims, 24 Drawing Sheets

(51) Int. Cl.
    *G01N 21/17*     (2006.01)
    *G01N 21/63*     (2006.01)
    *G01J 3/10*      (2006.01)
    *G01J 3/28*      (2006.01)
    *G01J 3/447*     (2006.01)

(52) U.S. Cl.
    CPC ....... *G01N 21/1717* (2013.01); *G01N 21/636* (2013.01); *G01N 2021/1725* (2013.01)

(56) References Cited

U.S. PATENT DOCUMENTS

| | | | |
|---|---|---|---|
| 4,496,839 A | | 1/1985 | Bernstein et al. |
| 4,676,642 A | | 6/1987 | French |
| 5,285,261 A | | 2/1994 | Dumoulin |
| 5,811,826 A | * | 9/1998 | Shirley .................. G01B 11/26 250/559.29 |
| 6,043,870 A | | 3/2000 | Chen |
| 6,175,421 B1 | | 1/2001 | Fuchs et al. |
| 6,543,288 B1 | | 4/2003 | Blouin et al. |
| 7,079,257 B1 | | 7/2006 | Kirkpatrick et al. |
| 8,743,363 B1 | | 6/2014 | Glennon |
| 2009/0069871 A1 | * | 3/2009 | Mahadevan-Jansen ...................... A61N 5/0618 607/89 |
| 2015/0276571 A1 | * | 10/2015 | Hajjarian ................ G01N 21/41 73/54.02 |
| 2016/0338623 A1 | * | 11/2016 | Tholl .................... A61B 5/1455 |

FOREIGN PATENT DOCUMENTS

WO   WO 2011/153973 A1   12/2011
WO   WO 2017/030652 A1   2/2017

OTHER PUBLICATIONS

Astrath, N. G. C., "Time-resolved thermal mirror for nanoscale surface displacement detection in low absorbing solids," *Appl. Phys. Lett.* 91: 191908 (2007).
Astrath, N. G. C., et al., "Unravelling the effects of radiation forces in water."*Nat. Commun.* 5(4363): 1-6 (2014).
Beck, J. V. "Large 'Time Solutions for Temperatures in a Semi-Infinite Body With a Disk Heat Source," *Int. J. Heat Mass Transfer* 24: 155-164 (1981).
Bialkowski, S. E., "Optical Principles for Photothermal Spectroscopy: Methods for Chemical Analysis", Chapter 4 (Wiley, 1996).
Boccara A. C. and Fournier, D., "Sensitive photothermal deflection technique for measuring absorption in optically thin media," *Opt. Lett.* 5: 377-379 (1980).
Briers, J. D. and Webster, S., "Laser Speckle Contrast Analysis (LASCA): A Nonscanning, Full-Field Technique for Monitoring Capillary Blood Flow," *J. Biomed. Opt.* 1:174-179 (1996).
Champion, J. L., "Shearographic Monitoring of Time-Dependent Thermoelastic Deformations," *Res Nondestr Eval* 13: 173-187 (2001).
Cikalova, U., et al., "Material Property/State Characterization by Laser Speckle Photometry," 18th World Conference on Nondestructive Testing, Apr. 16-20, 2012, Durban, South Africa.
Farahi, R.H., "Pump—probe photothermal spectroscopy using quantum cascade lasers," *J. Phys. D* 45 (125101): 1-7 (2012).
Georges, M., et al., "Electronic Speckle Pattern Interferometry At Thermal Infrared Wavelengths: A New Technique for Combining Temperature and Displacement Measurements," *Georges* (2011).
Goodman, J. W., "Speckle Phenomena in Optics: Theory and Applications" Chapter 3, (Roberts & Company), (2007).
Katz, O., et al.,"Non-invasive single-shot imaging through scattethig layers and around corners via speckle correlations," *Nat. Photonics* 8: 784-790 (2014).
Mërtiri, A., et al., "Mid-Infrared Photothermal Heterodyne Spectroscopy in a Liquid Crystal Using a Quantum," *Appl. Phys. Lett.* 101: 044101 (2012).
Olmstead, M.A., et al., *Appl. Phys. A* 32: 141 (1983).
Otteson, D., et al., "Detection of Surface Contamination Residue by Tunable Infrared Laser Imaging," (Sandia Report: SAND2001-8262) Sandia National Laboratories (2001).
Regan, C., et al., "Photothermal Laser Speckle Imaging," *Optics Letters* 39(17):5006-5009 (2014).
Rogers, J.A., et al., "Optical System for Rapid Materials Characterization With the Transient Grating Technique: Application to Nondestructive Evaluation of Thin Films Used in Microelectronics," *Appl. Phys. Lett.* 71:225 (1997).
Stolyarov, A.M., et al., "Photothermal Speckle Modulation for Noncontact Materials Characterization," *Optics Letters* 40(24):5786-5789 (2015).
Thompson, C.A., et al., "Imaging in Scattering Media by Use of Laser Speckle," *J. Opt. Soc. Am.* 14(9):2269-2217 (1997).
Yamaguchi, I., et al., "Detection of Photothermal Effect by Laser Speckle Strain Gauge," *Applied Optics* 36 (13):2940-2943 (1997).
Yamaguchi, I., et al., "Theory and Applications of Speckle Displacement and Decorrelation," Ch. 1 in *Speckle Metrology*, R. S. Sirohi ed. (Marcel Dekker) pp. 1-39 (1993).
Zalevsky, Z. et al., "Simultaneous remote extraction of multiple speech sources and heart beats from secondary speckles pattern," *Opt. Express* 17(24): 21566-21580 (2009).
Yalukova, O., et al., "Investigation of laser percussion hole drilling by use of speckle correlation," *Applied Optics*, 44(30): 6338-6344 (2005).
Hiroi, T., et al., "Solder Joint Inspection Using Air Stimulation Speckle Vibration Detection Method and Fluorescence," *IEICE Transactions on Information and Systems*, No. 10: pp. 1144-1151 (Oct. 1993).
Rogers, J. et al., "Optical System for Rapid Materials Characterization with the Transient Grating Technique: Application to Non Destructive Evaluation of Thin Films Used in Microelectronics," American Institute of Physics, 71(2): 225-227 (1997).
International Search Report and the Written Opinion for PCT/US2016/038310, entitled: "Sensing Targets Using Photothermal Speckle Detection," dated Oct. 13, 2016.
Notification Concerning Transmittal of International Preliminary Report on Patentability for International Application No. PCT/US2016/038310, entitled: "Sensing Targets Using Photothermal Speckle Detection," dated Mar. 1, 2018.

* cited by examiner

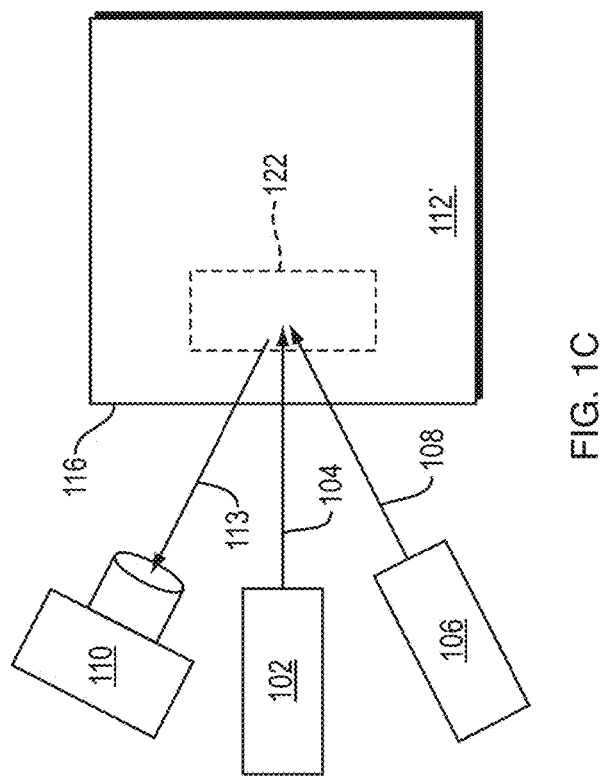

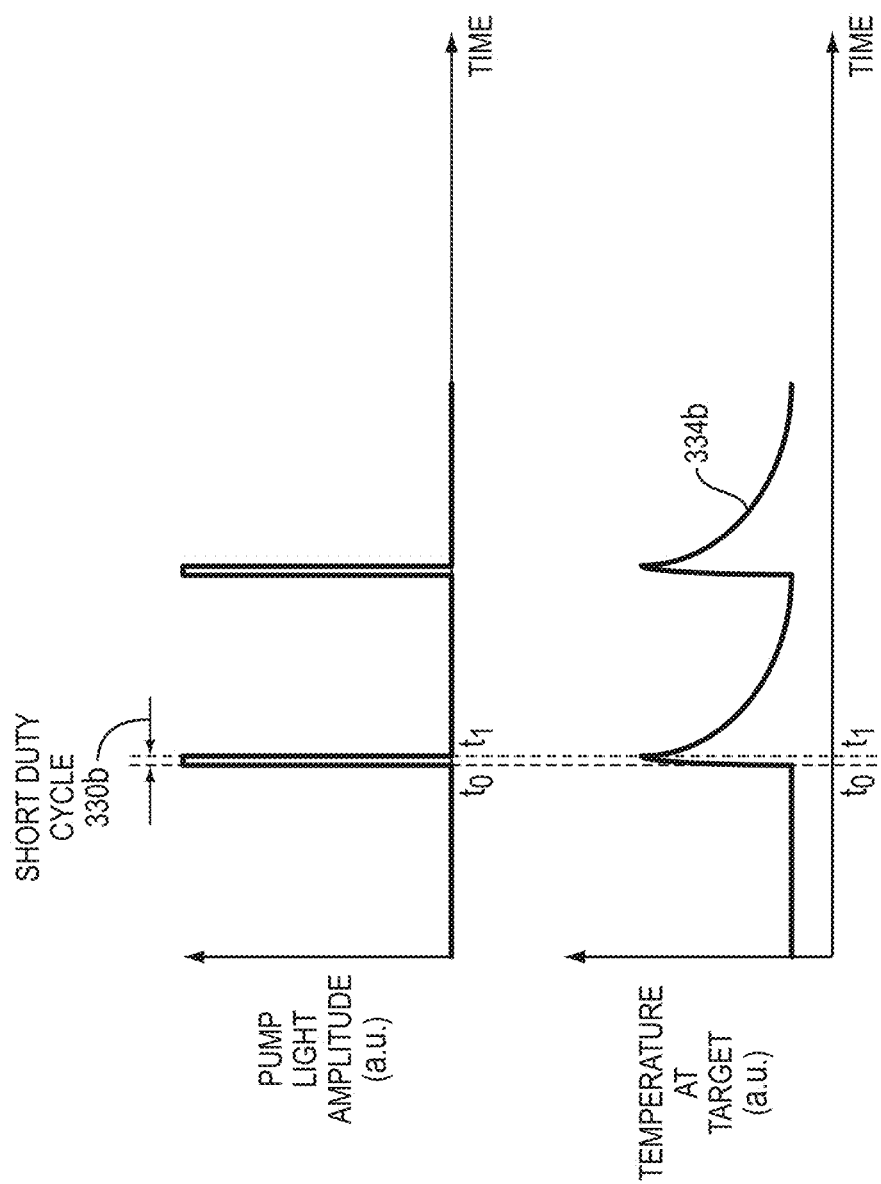

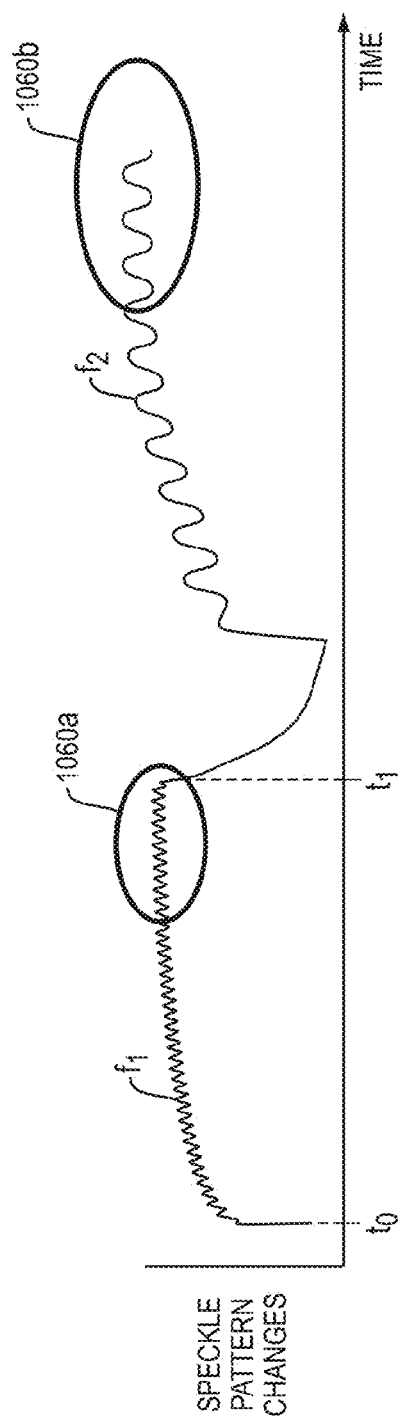
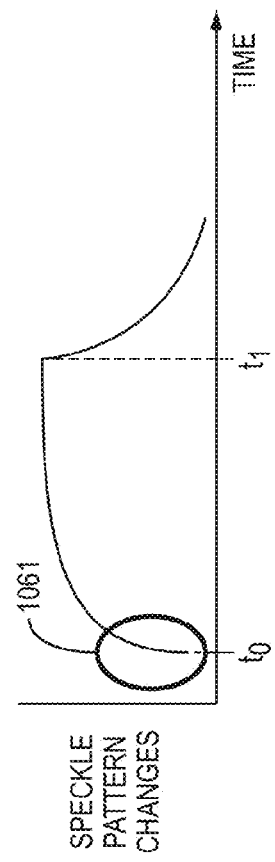
FIG. 10A
FIG. 10B

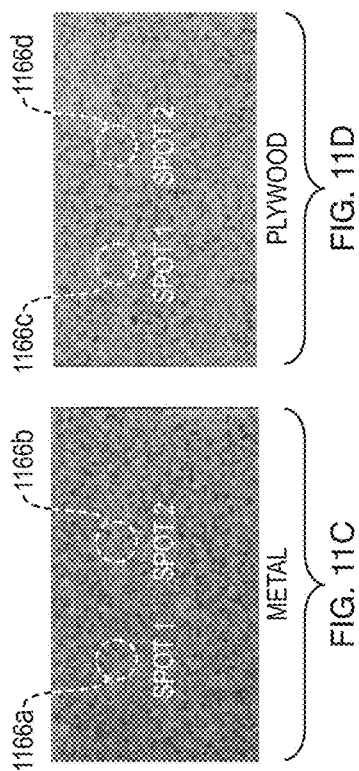
FIG. 11C
FIG. 11D
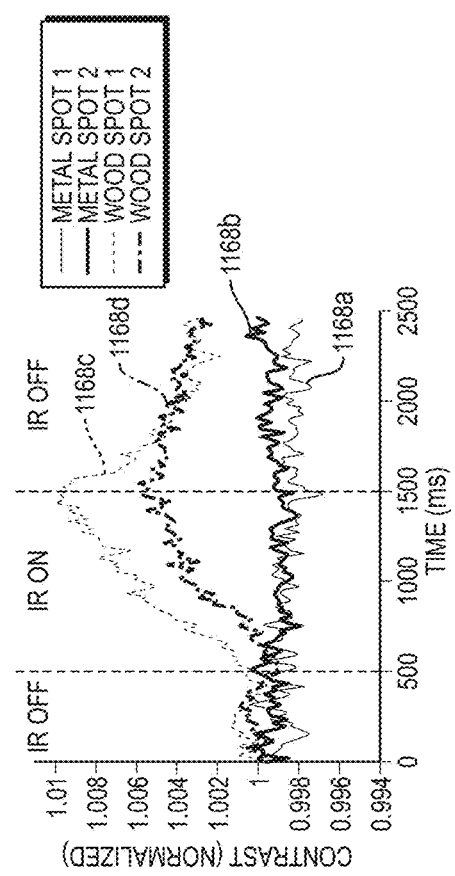
FIG. 11E

DEVICES AND METHODS FOR SENSING TARGETS USING PHOTOTHERMAL SPECKLE DETECTION

RELATED APPLICATIONS

This application claims the benefit of U.S. Provisional Application No. 62/207,720, filed on Aug. 20, 2015. The entire teachings of the above application(s) are incorporated herein by reference.

GOVERNMENT SUPPORT

This invention was made with Government support under Contract No. FA8721-05-C-0002 awarded by the U.S. Air Force. The government has certain rights in the invention.

BACKGROUND

Various techniques have been used for non-contact sensing of target materials. One class of existing techniques can be referred to as reflectance spectroscopy. Infrared (IR) reflectance spectroscopy directly detects back-scattered radiation at the pump wavelength, which can also be used to determine optical properties of the target material surface.

A second class of techniques that probe infrared absorption of target materials are alternative photothermal approaches that involve measurement of changes in the thermal emission of the surface (measured using infrared radiometry) as a function of incident wavelength. These techniques can measure either the total change in thermally radiated power associated with the temperature rise of the surface or the change in the spectrum of the blackbody emission, modulated by the characteristic emissivity of the surface material.

SUMMARY

Existing techniques for non-contact analysis of target materials suffer from a variety of drawbacks. Some of these drawbacks include the difficulty, expense, atmospheric absorption, and detector noise associated with detecting long-wavelength infrared (LWIR) light. For example, LWIR sensors can require cryogenic temperatures to reduce sensor noise sufficiently. Other disadvantages include the complexity of interpreting scattering spectra, limited spatial resolution and signal-to-noise ratios (SNRs), and limited sensitivity.

Embodiments disclosed herein overcome drawbacks of existing techniques by providing high-sensitivity, non-contact detection of target materials, even without the need for infrared sensing or cryogenic sensor operation. At least two wavelengths can be used, including pump and probe wavelengths. The pump wavelength can be in the near-infrared (near-IR), for example. Embodiments do not depend on backscatter of the pump wavelength for operation. A probe wavelength can be visible, for example, and can be selected to be non-absorbing at the target material and to produce a speckle pattern whose variation as a function of pump light modulation can be monitored and analyzed to distinguish between different target materials or classes of materials and to identify materials based on material properties such as absorption spectra and thermal diffusivity. IR absorption spectra can be obtained, for example, without direct detection of IR radiation and without a thermal camera. Embodiments can be used in a variety of applications, including remote sensing of target materials.

In one embodiment, a device, and a corresponding method, includes a pump light source configured to be modulated at a pump modulation and to irradiate a target specimen. The device can also include a probe light source arranged to generate a speckle pattern from the target specimen, as well as a sensor configured to detect changes in at least one of position and intensity of one or more speckle lobes (e.g., locations of constructive interference in an intensity pattern produced as a result of a diffuse reflection of coherent light) of the speckle pattern having correlation with the pump modulation. The device can also include a correlator that is configured to perform a frequency analysis to determine correlation of the changes in at least one of position and intensity of the one or more speckle lobes with a frequency of the pump modulation. The pump modulation can be on a timescale shorter than a timescale of blurring of the speckle pattern, and the sensor can be configured to detect the changes in at least one of position and intensity on a timescale shorter than the timescale of blurring of the speckle pattern.

The device can also include a processor, and the processor can be configured to determine an absorption spectrum of the target specimen based on the changes in at least one of position and intensity of the one or more speckle lobes correlated with the pump modulation. The processor can also be configured to determine a thermal diffusivity of the target specimen based on the changes in at least one of position and intensity of the one or more speckle lobes.

The processor can be further configured to identify a material class of the target specimen based on the absorption spectrum and to identify the material class independent of an optical property of a surface of the target specimen.

The sensor can be further configured to detect changes in at least one of position and intensity of the one or more speckle lobes during or after a particular duty cycle of the pump modulation. The duty cycle of the pump modulation can be short in comparison with a thermal diffusion time of the target specimen.

The pump modulation can be a light amplitude modulation, and the sensor can be further configured to detect the changes in at least one of position and intensity of the one or more speckle lobes as a function of the light amplitude modulation. The pump modulation can also be a light polarization or wavelength modulation, and the sensor can be further configured to detect the changes in at least one of position and intensity of the one or more speckle lobes as a function of the light polarization or wavelength modulation, respectively. The pump light source can be further configured to irradiate the target specimen with a plurality of wavelengths of pump light simultaneously. The plurality of wavelengths can be at different locations of the target specimen or at least partially overlapping at the target specimen. The pump light source can be further configured to modulate light amplitude of the plurality of wavelengths at respective, mutually distinct light amplitude modulation frequencies.

The pump light source can be configured to irradiate the target specimen with pumped light of a fixed wavelength, with pump modulation being pump light amplitude modulation, and the pump light source can be further configured to output the light at a plurality of amplitude modulation frequencies. The sensor can be configured to detect changes in at least one of position and intensity of the one or more speckle lobes correlated with the plurality of frequencies of the light amplitude modulation. The processor can be further configured to determine a thermal diffusivity of the target specimen based on the changes in at least one of position and intensity of the one or more speckle lobes correlated with the plurality of frequencies of the light amplitude modulation. The pump modulation of the pump light source can have a time profile that is sinusoidal or rectangular. The pump light source can be further configured to generate a speckle pattern from a given region of the target specimen, and the sensor can be further configured to detect changes in at least one of position and intensity of the one or more speckle lobes at different positions in the given regions of the target specimen. The probe light source can be further configured to generate the speckle pattern from a position inside the target specimen, the probe light passing through an outer surface of the target specimen to the position inside the target specimen.

The sensor can include an array of detector elements. The detector elements can be photomultiplier tubes (PMTS), CCD array elements, CMOS array elements, photodiode array elements, or photosensitive fibers. The pump light source can be a pulsed laser. The pump light source can also be a continuous wave (CW) laser, and the device can further comprise a light modulator configured to modulate amplitude of light from the pump light source. The probe light source can be configured to have a wavelength that is substantially non-absorbing at the target specimen. A wavelength of the pump light source and a wavelength of the probe light source can be mutually distinct. The pump light source can be further configured to be tunable in wavelength over a region of wavelengths overlapping with an absorption region of the target specimen. The pump light source can be an infrared laser and can have a wavelength in a range of about 8 µm to about 12 µm. The infrared laser can be at least one of a $CO_2$ laser, a quantum cascade laser, and a dye laser. The pump light source can also be an ultraviolet or visible laser. The processor can be configured to determine a thermal diffusivity of the target specimen based on the changes in at least one of position and intensity of the one or more speckle lobes correlated with the pump modulation.

In another embodiment, a method, and corresponding device, includes modulating a pump light source at a pump modulation and irradiating a target specimen with light from the pump light source. The method can also include generating a probe light speckle pattern from the target specimen and detecting changes in positions of one or more speckle lobes of the speckle pattern having correlation with the pump modulation.

In yet another embodiment, a device includes means for modulating a pump light source and means for irradiating a target specimen with light from the pump light source. The device can also include means for generating a probe light speckle pattern from the target specimen and means for detecting changes in positions of one or more speckle lobes of the speckle pattern having correlation with the pump modulation.

In still a further embodiment, a method, and corresponding device, includes irradiating a target specimen with light from a pump light source, as well as observing a probe light speckle pattern based on light from a probe light source reflected from the target specimen. The method can also include determining a material property of the target specimen by analyzing changes in images of the probe speckle pattern as a function of the irradiation with the pump light source.

In yet a further embodiment, a device, and corresponding method, includes a pump light source configured to irradiate a target specimen and a sensor configured to observe a probe speckle pattern based on light from a probe light source reflected from the target specimen. The device can also include a correlator configured to determine a material property of the target specimen by analyzing changes in images of the probe speckle pattern as a function of the irradiation with the pump light source.

The material property can be an absorption spectrum or portion thereof, a thermal diffusivity or class of thermal diffusivities, or a general material class of the target specimen. The pump light source can be configured to be modulated periodically, and the periodic modulation can include either a single modulation frequency or a plurality of modulation frequencies. The probe light source can be an ultraviolet or visible light source.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1C illustrates and embodiments device configured to generate a speckle pattern from a position inside a target specimen.

FIG. 3B illustrates pump light duty cycles that are short with respect to a thermal diffusion time of a target specimen and a timeframe of blurring of a speckle pattern.

FIG. 10A illustrates example speckle pattern changes for frequency-based measurements obtained according to embodiment methods.

FIG. 10B is a graph illustrating example speckle pattern changes expected for time-based measurements.

FIGS. 11C-11D are photographs indicating measurement positions for metal and plywood surfaces, respectively, painted to look the same.

FIG. 11E is a graph illustrating contrast as a function of time for the measurement positions indicated in FIGS. 11C-11D.

DETAILED DESCRIPTION

Figure 1A:
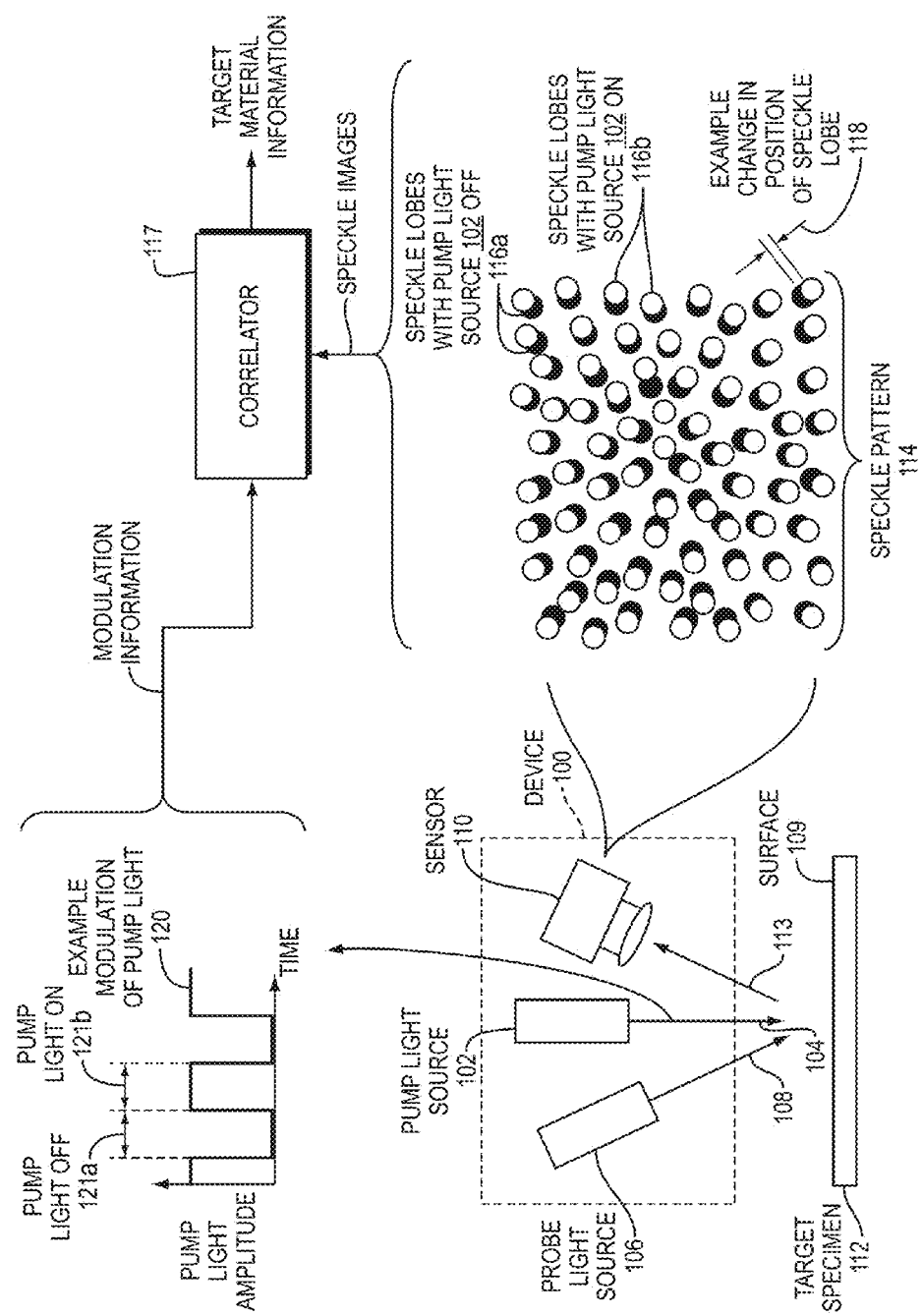
FIG. 1A is a schematic illustration of an embodiment device that can be used for remote sensing of target specimens.

A description of example embodiments of the invention follows.

The current disclosure describes methods and devices for obtaining optical absorption information for materials on surfaces in a non-contact manner using laser illumination. Embodiments can be used for detecting contamination of surfaces with hazardous materials (e.g. explosives or chemical warfare agents) or for doing material identification (e.g., of paints or other coatings). Embodiment devices and methods can also be used to nondestructively test surfaces for variation in optical absorption, thermal diffusivity, and to detect subsurface features that cause variation in the response of the surface to the absorption of illuminating radiation.

Embodiments can take advantage of photothermal modulation of a laser speckle pattern emanating from a surface of a target specimen, which is also referred to herein as "photothermal speckle modulation" (PSM). The approach can include simultaneous illumination of the target with at least two separate light wavelengths from, for example, laser light sources. The first laser wavelength, called the "pump" wavelength, can be absorbed at the surface of the target specimen material of interest. Many pump wavelengths can be used, and it is particularly advantageous to use pump wavelengths in the long-wave-infrared (IR) (7-12 µm in wavelength), where many materials of interest have highly specific absorption signatures. However, in various embodiments, other pump wavelength ranges can be used, such as near infrared or other wavelength regions in which materials of interest exhibit absorption. When the pump wavelength illuminates an absorbing target surface, that surface will be heated by the absorbed radiation. It is then useful to read out the heat deposition on the surface, i.e., evaluate the degree of absorption and response. This readout can be accomplished by a second laser illumination, called the "probe." The probe laser can be sufficiently coherent to generate a laser speckle pattern from the surface.

Laser speckle pattern denotes a spatially non-uniform scattering pattern that results from illumination of a rough surface with coherent light, the surface being rough in comparison with the probe laser wavelength. The laser speckle pattern from a target surface is highly dependent on the details of the surface roughness and material refractive index at the surface. By heating the surface with the pump laser, the appearance of the laser speckle from the surface due to thermal expansion and index change can be altered, and the change in speckle as the pump laser is modulated can be detected. This change in speckle relates to the absorption of the pump wavelength, and, therefore, can be used to understand the optical absorption properties of the surface at the pump wavelength. By tuning the pump wavelength and performing this measurement at each wavelength, the optical absorption spectrum of the target surface can be measured.

This photothermal speckle process offers a number of advantages over existing techniques for probing the infrared absorption features of a surface One class of existing techniques can be referred to as reflectance spectroscopy. IR reflectance spectroscopy directly detects back-scattered radiation at the pump wavelength, which can also be used to determine the optical properties of the surface. The advantages of photothermal speckle modulation (PSM) as disclosed herein are particularly apparent for wavelength combination including a pump wavelength in the long wave infrared (LWIR, e.g., 7-12 µm) range to match absorption features of interest and a probe wavelength in the visible-SWIR (0.5-1.5 µm).

Key advantages of PSM compared to detecting backscattered LWIR include the following. No LWIR photodetector is required. In general, LWIR photodetectors are expensive, have high noise, and require cryogenic temperatures to operate. Visible and SWIR photodetectors are low cost and high performance, and they operate at or near room temperature, because they can detect much higher photon energies, which is fundamentally less challenging. Direct sample absorption can be detected, rather than backscatter. Absorption signatures are more straightforward to interpret compared to scattering signatures. The LWIR illumination only needs to propagate from the transmitter to the target, while any visible or SWIR light used a probe, for example, propagates both from the transmitter to the target, and then back to the receiver (sensor). LWIR absorption in the atmosphere is typically much greater than optimally-selected visible or SWIR wavelengths. In addition to the absorption information, by adjusting the rate of modulation of the pump beam and looking for the associated modulation transfer to the probe beam, information about the thermal time constants of the surface can be accessed. This may provide an additional dimension of information for material identification or for detecting subsurface features. Thus, embodiment methods and devices can take advantage of using visible or SWIR wavelengths for a probe light source, with advantages that include lower atmospheric absorption and the ability to detect probe light using sensor arrays that are relatively inexpensive and easy to use.

Other advantages include the following. Embodiment devices and methods can also be highly sensitive. If a probe laser is chosen that has low noise at the modulation frequency of the pump beam, and if appropriate probe intensity is available, then the probe return can be chosen to be large compared to detector noise (eliminating the detector noise's effect on sensitivity) and the shot noise in the probe beam can be made smaller than the modulation transferred from the pump beam. This approach can then reach the ultimate sensitivity limit: the shot noise associated with the absorption process at the target. For applications such as long range standoff detection where there are practical constraints on the transmit/receive aperture size, this approach can lead to improved spatial resolution on target because the probe wavelength can be significantly shorter than the pump wavelength. For example, if the pump wavelength is 10 µm and the probe (readout) wavelength is 0.5 µm, a common transmit/receive aperture could resolve ~20×20 subregions within the 10 µm illuminated spot. Higher resolution material ID on target potentially reduces signature clutter and improves discrimination in targets with non-uniform material composition versus position.

A second class of techniques that probe infrared absorption are alternative photothermal approaches that involve measurement of changes in the thermal emission of the surface (measured using infrared radiometry) as a function of incident wavelength. These techniques can either measure the total change in thermally radiated power associated with the temperature rise of the surface or they can measure the change in the spectrum of the blackbody emission, modulated by the characteristic emissivity of the surface material.

PSM imaging has advantages relative to thermal radiance measurements including the following. Using a vis-SWIR probe wavelength results in higher spatial resolution. Further, use of visible and SWIR focal planes in comparison with LWIR focal planes has the advantages described above. Also, imaging can be sensitive to much smaller temperature changes with PSM than with thermal radiance approaches.

In addition to applications in trace detection, embodiment devices and methods can have applicability to a wide range of non-destructive analysis, where material composition, subsurface features, and thermal time constant are of interest and can be obtained remotely and with high sensitivity. For example, applications can include inspection of composites, ceramics and other materials used in manufacturing of electronics, aircraft, and other fields, or analysis of pharmaceutical and chemical manufacturing process lines.

Embodiment measurement devices and techniques described herein are fundamentally different from an existing photothermal speckle technique used to image blood flow. The existing technique relies on measuring speckle blurring (i.e., a decrease in contrast of the speckle image caused by an increase in motion of scattering particles due to a photothermal excitation. In contrast to the existing blood flow imaging technique, and in accordance with embodiments described herein, the speckle contrast can remain nearly constant while small changes induced by modulation of pump light can be correlated with the modulation to obtain target material information. A modulation transfer technique can be applied to measure speckle fluctuations correlated to the pump modulation frequency. For some embodiments, the pump modulation can occur on time scales shorter than a time scale for longer-term speckle blurring due to thermal absorption at the target surface or to environmental effects, for example. Furthermore, based on using detection and imaging of speckle, embodiments described herein can enable spectroscopic target materials identification or distinguishing targets based on material properties, which have not been demonstrated with other photothermal speckle measurement techniques.

FIG. 1A illustrates a device 100 that includes a pump light source 102, a probe light source 106, and a sensor 110. The pump light source 102 is configured to be modulated at a pump modulation (here, a light amplitude modulation 120) and to irradiate a target specimen 112 with pump light 104. In some embodiments described hereinafter, the pump light source can be configured to be tunable in wavelength over a region of wavelengths overlapping with an absorption region of the target specimen, such as absorption peak. Infrared pump light source wavelengths can be particularly useful, since many potential targets of interest have absorption regions in the infrared wavelengths. For example, a pump light source can have a wavelength in a range of about 8 µm to about 12 µm, for example. A pump light source can be an infrared laser such as a $CO_2$ laser, a quantum cascade laser, a diode laser, or a dye laser. Furthermore, in other embodiments, a pump light source can be an ultraviolet or visible laser where there is sufficient absorption of these wavelengths by potential target specimens, such that probe light can be deflected due absorption of the pump wavelength by the target.

The probe light source 106 is arranged to generate a speckle pattern from the target 112 by irradiating the target 112 with probe light 108. In particular, the probe light 108 gives rise to a speckle pattern 114 that is generated from the target 112. As understood in the art of optics, speckle lobes can be observed in light with at least some coherence that is diffusely reflected from a target. Such speckle lobes are essentially locations of constructive interference in an intensity pattern produced as a result of the diffuse or partially diffuse reflection. Moreover, in accordance with embodiments described herein, variation in position of the speckle lobes due to thermal variation in a target due to turning pump light source on or off can be exploited to determine an absorption spectrum or other property of a target specimen to identify the target specimen, even remotely.

The sensor 110 is configured to detect changes in position of one or more speckle lobes of the speckle pattern 114. This detection can also be referred to as observing the probe speckle pattern based on light from the probe light source reflected from the target specimen. Changes 118 in positions of the one or more speckle lobes have correlation with the pump modulation. In some embodiments, a center position of each speckle lobe may be tracked over time, for example. Then a Fourier analysis may be performed to determine frequency dependence of each speckle lobe, particularly any frequency component that is correlated with the pump modulation. However, if pixels in a detector array are analyzed over time, the pixel values or light intensities reflected by the pixel values will have the same frequency dependence as the speckle lobe positions. Thus, a potentially faster, and less computationally intensive, approach to determining correlation of speckle lobe changes with pump modulation can include performing frequency analysis (e.g., Fourier analysis) of detected light intensities (represented by sensor pixel values). This more direct, pixel intensity-based approach is further described hereinafter.

It should be understood that, where frequency analysis or correlation of pixel values (detected light intensities) is described herein, analysis or correlation of positions of speckle lobes on a pixel array, for example, may be performed instead of, or in addition to, the analysis or correlation of pixel values. Furthermore, it will be understood that changes in positions of speckle lobes result in changes of pixel values (light intensity values) at various pixel positions. Therefore, changes in position can be detected by reference to light intensities measured in pixel values, for example. Therefore, changes in position and changes in intensity may also be referred to interchangeably herein. Nevertheless, changes in speckle lobe intensity can also occur independent of any motion of the speckle lobe at the detector (pixel) array. For example, in some cases, modulation of pump light incident at the target surface to be analyzed can result principally in intensity changes of speckle lobes, instead of motion, due to interference effects resulting from the target surface flexing, for example. These intensity changes also can be correlated with the pump modulation according to embodiment devices and methods.

In some embodiments, the sensor 110 is configured to detect the changes in position or intensity (or both) of the speckle lobes on a timescale shorter than a timescale of blurring of the speckle pattern, as illustrated hereinafter. In some embodiments, such as that shown in FIG. 1B, the sensor is a camera with a pixel array. In various embodiments, a sensor can include either a single detector element, such as a photomultiplier tube (PMT) or an array of detector elements, such as CCD array elements, CMOS array elements, photodiode array elements, or photosensitive fibers.

The pump light source 106 is configured to be modulated at a pump modulation. FIG. 1A also illustrates an example modulation 120 of the pump light source 102. As used herein, "modulation" indicates a periodic or cyclic change in light 104 from the pump light source 102 that occurs over two or more cycles. In particular, the pump light amplitude of the pump light 104 can be periodic and can follow a square wave pattern with a zero offset, as illustrated in FIGS. 10A-10B, for example. However, in other embodiments, the pump light source modulation is defined by a sine wave, as illustrated in FIG. 2A, or another functional pattern. Modulation of the pump light source can be modulation of, for example, wavelength or polarization of the pump light 104 instead of amplitude modulation. In FIG. 1A, the pump light source 102 is off, for zero pump light amplitude (zero offset) during a time period 121a, and the pump light source is on during a time period 121b.

Figure 11A:
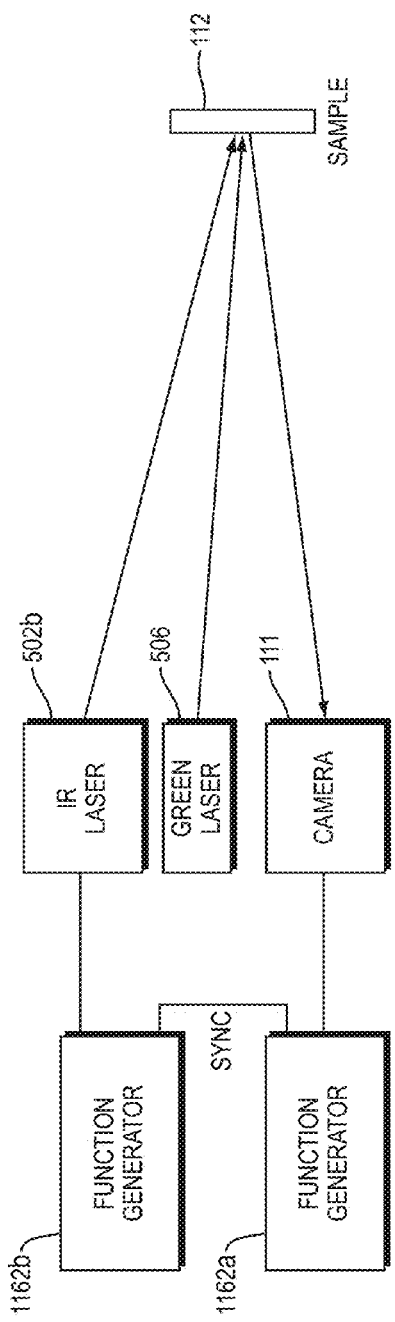
FIG. 11A is a schematic diagram illustrating a device configured to perform time-based PSM measurements.
Figure 11B:
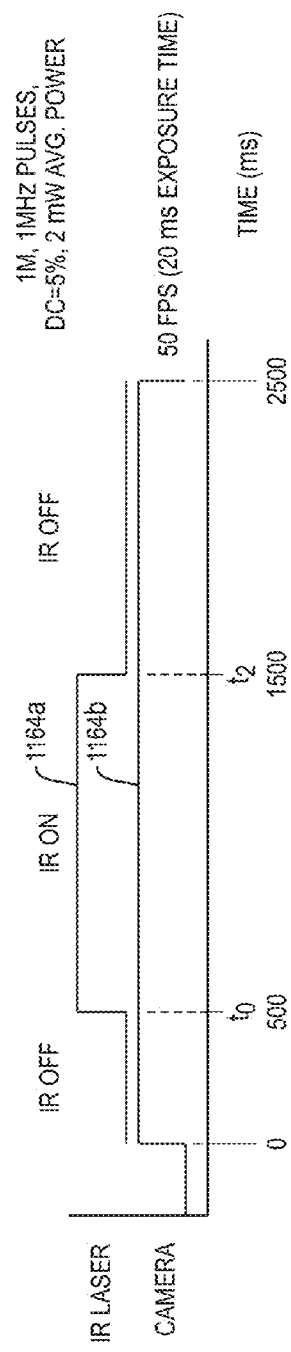
FIG. 11B is a graph illustrating relative on and off times for operating the pump laser and the camera illustrated in FIG. 11A with a pump laser duty cycle that is long in comparison with a thermal diffusion time of the target sample.

While the pump light source can be modulated in many embodiments, in other embodiments, such as those illustrated in FIG. 10B and FIGS. 11A-11B, a pump light source need not be an "modulated," but instead can be simply turned on and then off at appropriate times without a periodic change. For example, the pump light can be turned on or off at certain times with respect to a camera sensor detecting images, for example. The pump light source is further configured to irradiate the target specimen 112 with the pump light 104 by directing the pump light to the target specimen 112. In some embodiments, the pump light source 102 is a laser that is pointed at the target specimen. In some embodiments, a non-laser pump light source can be used, and appropriate optical components can be used to direct and focus the pump light 104 to the surface of the target specimen. The probe light 108 and pump light 104 typically overlap completely or partially at the surface 109 of the target specimen, such that absorption of pump light by the target specimen produces the largest possible heating distortion of the surface 109 of the target, and, consequently, the greatest deflection of the probe light 108. While very short duty cycles can be provided by, for example, pulsed laser pump light sources, the light output from continuous wave (cw) lasers can also be modulated using an optical chopper, for example, that is separate from the cw laser.

FIG. 1A also illustrates an example speckle pattern 114 generated by the probe light source 106 from the target 112. In particular, individual speckle lobes 116a (shaded relatively darker) are shown during the time 121a when the pump light source 102 is off or the light amplitude is at a minimum on the curve 120. The speckle pattern 114 also shows spatially shifted speckle lobes 116b (shaded relatively lighter) during the time 121b when the pump light source 102 is on (pump light amplitude shown in the curve 120 is at a maximum). An example change 118 in position of a speckle lobe is also shown in the speckle pattern 114, and the difference in position is between the time when the pump light source is on and the pump light source is off. The changes 118 in position of the speckle lobes have correlation with the pump modulation 120 because the positions of the speckle lobes change each time the pump light is turned on or off in the example modulation 120. The positions of the speckle lobes change in response to the variation or modulation in the pump light. Other changes in positions or intensities of the speckle lobes may also occur independently of pump light modulation. For example, air currents between the pump and probe light sources and the target or between the target and the sensor can affect light wavefront and the speckle pattern. Furthermore, some thermal changes in the target specimen 112 can be independent of pump light modulation and can cause other changes in positions or intensities of speckle lobes that do not have any correlation with pump modulation.

As described in more detail hereinafter, some embodiments include capability to determine the particular correlation of the changes in speckle lobe positions with pump modulation. In FIG. 1A, a correlator 117 can receive information about pump light modulation (e.g., frequency of modulation) and speckle pattern 114 images over time. The correlator 117 can include a processor that can perform a Fast Fourier Transform (FFT) on the recorded variation of speckle pattern position with time to determine which changes occur at the same frequency as the pump light modulation 120. Thus, the correlator 117 can perform a frequency analysis to determine the correlation of the changes in positions of the speckle lobes with the pump modulation frequency. Furthermore, in some embodiments, a correlator can include a lock-in amplifier can be used to selectively amplify frequency components in the speckle pattern position changes that have correlation with the pump light modulation, for example.

Furthermore, a correlator as illustrated in FIG. 1A can have other functions, such as determining a material property of the target specimen based on the changes in positions of the speckle lobes. For example, in some embodiments, a material property that is determined by the correlator can include a material class (e.g., metal, plastic, composite, etc.), absorption spectrum, thermal diffusivity, or CTE. The correlator 117 (e.g., processor therein) can be configured to identify a material class of the target specimen based on, for example, absorption spectrum or thermal diffusivity or other material properties, which can affect how strongly the positions of the one or more sparkle lobes change in response to pump light modulation. Determination of material properties using embodiment devices and methods is further included hereinafter in the description of FIG. 6.

Thus, the correlator 117 can be configured to output information about the target material, such as a class of materials (e.g., plastic, metal, etc.) to which the target specimen belongs. Even in other embodiments in which pump light is not modulated, a material property of the target specimen, such as a class of materials or a class of thermal diffusivities of the target specimen can be determined by analyzing changes in images of the probe speckle pattern as a function of the irradiation with the pump light source. In some embodiments, analyzing changes in the probe speckle pattern as a function of the irradiation with the pump light source includes determining a correlation of the changes with the pump modulation. However, in other embodiments, analyzing the changes as a function of the pump light irradiation includes only determining the change to speckle pattern images between the pump light being turned on and then off.

Pump light 104 absorbed by the target 112 causes a temperature rise the target specimen 112, and the target consequently expands, causing a surface 109 of the target to be distorted. Co-incident onto the same area or spot of the target as the pump light 104 is the probe light 108. Scattering from the surface 109 leads to light 113 that gives rise to the speckle pattern 114 that is detected by the sensor 110. In one embodiment, for example, the pump light source 102 can be an infrared laser or other infrared source of light that can be absorbed by the target 112. One example wavelength is 7.8 μm, and one example range of modulation frequencies is 11-20 Hz. In other embodiments, modulation frequencies can be higher, such as a few hundred or a few thousand Hertz, or lower. In some embodiments, the probe light source 106 can output light 108 that is in the visible wavelength range, such as, for example, 532 nm. The speckle pattern changes (motion and/or changes in intensity) can be periodic with the same frequency as the modulation of the pump light source 102.

Figure 1B:
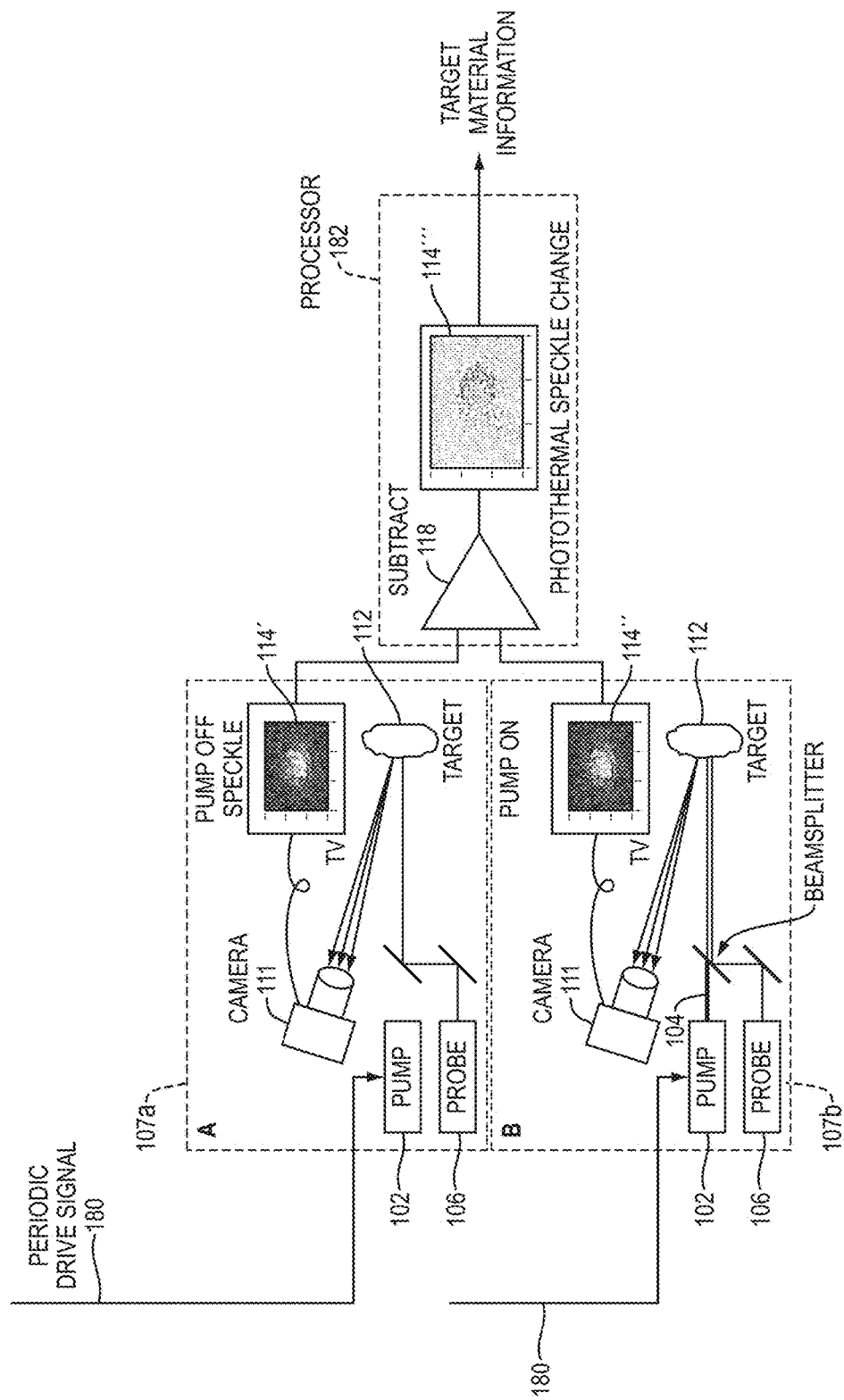
FIG. 1B illustrates an embodiment device in which images with the pump light source on and off are subtracted from each other to obtain a photothermal speckle change.

FIG. 1B is a schematic illustration of an embodiment of the device 100 illustrated in FIG. 1A. A two-color laser system with both pump and probe wavelengths that can simultaneously illuminate the target 112. A camera 111 reads out the target speckle image in a non-contact manner. It is preferable for the pump and probe wavelengths to be mutually distinct, such that the probe wavelength is not absorbed by the target specimen, whereas the pump wavelength can be absorbed, at least as a function of wavelength. Speckle pattern images 114" and 114' with and without, respectively, the pump light illuminating the target, are subtracted at 118 to obtain a photothermal difference image 114' whose difference is related to the pump absorption. The subtraction can take place in, for example, a correlator such as the correlator 117 illustrated in FIG. 1A, or any processor capable of performing calculations on image data. This modulation can be done at low speed with subsequent frames of a video imager, or at high speed (MHz or faster) using a high frequency detector and lock-in amplifier or other more sophisticated signal processing.

High speed differencing can be used to remove artifacts due to motion at slow timescales, e.g. motion of the target or atmospheric perturbations on the path from transmitter to target or from target to sensor. Motion of the target or atmospheric perturbations can result in blurring of the speckle pattern that is unrelated to the target specimen absorbing pump light. Ultimately, a focal plane capable of high speed frame differencing can provide simultaneous wide field imaging coverage and high frequency modulation capability, though such imagers may be beyond the present commercial state-of-the-art.

In FIG. 1B, the sensor is a camera 111 that is configured to be sensitive only to light from the probe 106. In box 107a, a speckle pattern 114' is illustrated being provided by the camera 111 at a time when the pump light 104 is off. In contrast, the box 107b illustrates a speckle pattern image 114" obtained from the camera 111 when the pump light source 102 is on and providing pump light 104 to illuminate the target 112. Alternating recordings of the speckle pattern 114' and 114" are thus obtained with the pump light source 102 on and off. The images 114' in 114" are subtracted electronically at 118 to produce a speckle pattern image change 114 that is related to the absorption of the pump light by the target 112. In embodiments illustrated hereinafter, the values from individual pixels of the camera 111 over time are separately analyzed by means of a Fast Fourier Transform (FFT), and then the FFTs from individual pixels are averaged to produce an average FFT spectrum. Furthermore, in other embodiments, a high-speed single point detector that samples a small portion of the speckle pattern can be used. In the case of a high-speed single point detector, a higher frequency modulation of the speckle pattern can be read and recorded than in the case of the camera 111.

FIG. 1C illustrates an embodiment in which the probe light source 106 is configured to generate the speckle pattern from a position 122 inside a target specimen 112'. The probe light 108 passes through an outer surface 116 of the target specimen 112' to the position 122 inside the target specimen. Light 104 from the pump light source 102 illuminates, and is absorbed in, the region 122, and reflected light 113 is captured by the sensor 110. The embodiment of FIG. 1E can be useful, for example, where the surface 116 of the target 112' is transparent to the pump light 104 and probe light 108, but where some pump light 104 is absorbed in the region 122, and some probe light 108 produces a speckle in the region 122 that can be detected by the sensor 110. For example, this technique can be applied for subepidermal imaging applications, wherein the pump and probe light wavelengths can be chosen to transmit through the outer skin layer but be absorbed by vascular layers beneath the skin.

Figure 1D:
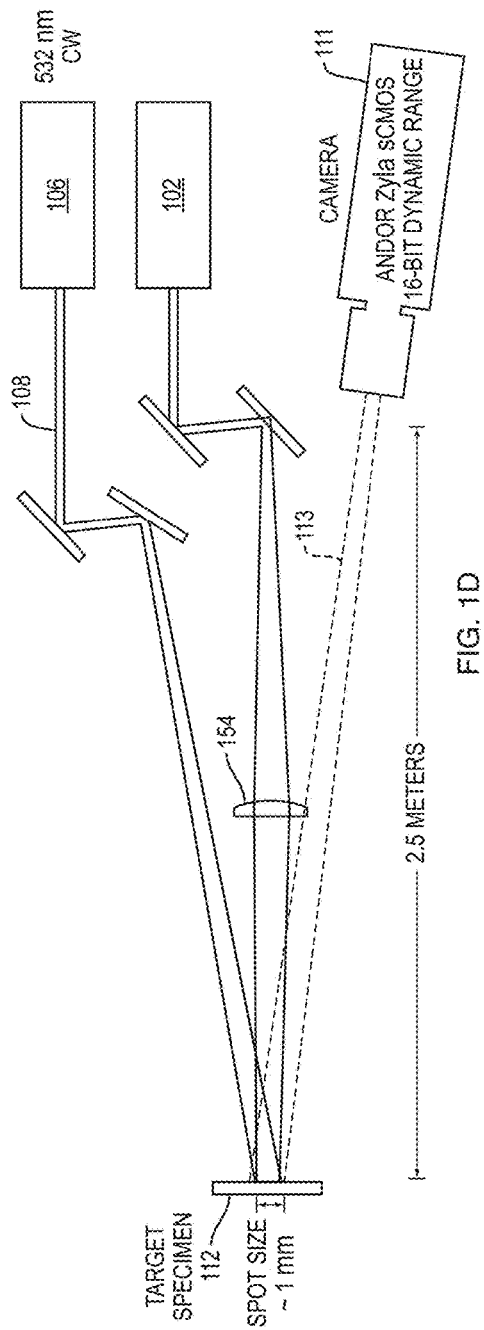
FIG. 1D is a schematic diagram illustrating an embodiment device used for testing, the device incorporating a quantum cascade laser (QCL) pump light source and a complementary metal-oxide semiconductor (CMOS) 16 bit camera sensor.

FIG. 1D is a schematic diagram illustrating an embodiment device used for testing. The device incorporates a quantum cascade laser (QCL) pump light source 102 tunable over wavelengths ranging from 7.4 to 8.4 μm. The device also incorporates an ANDOR Zyla complementary metal-oxide semiconductor (CMOS) 16 bit camera sensor 111. The target specimens were positioned in a non-contact manner, roughly 2.5 meters from the pump laser source and the light collection optics. Both the pump and probe laser powers were in the range of 1-10 milliwatts. A 160 mm focal length lens 154 with f-stop set to 4 was used to collect the scattered probe beam light and direct it towards the CMOS camera. In other embodiments, with appropriate collection optics, distances can be much greater than 2.5 meters, enabling a wide variety of remote sensing applications.

Figure 1E:
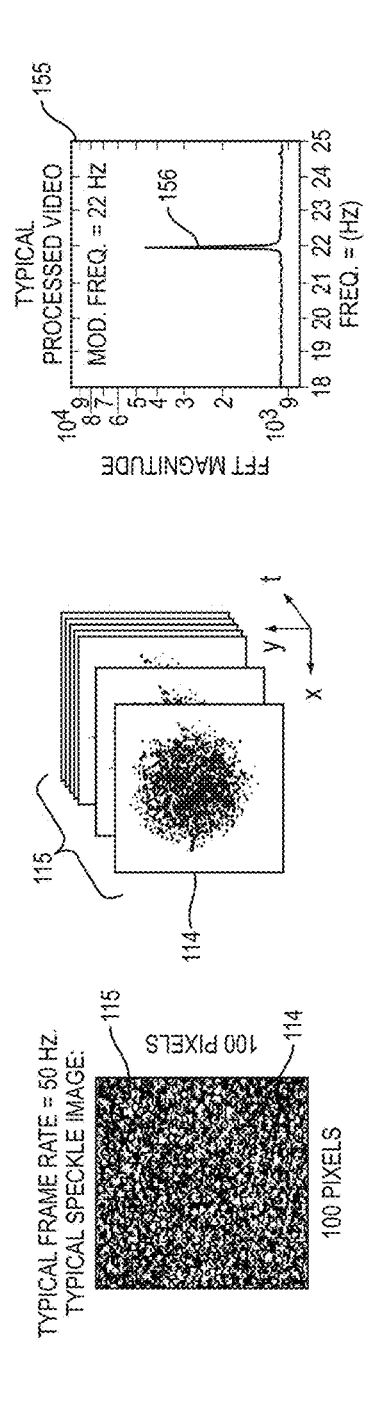
FIG. 1E includes speckle images and a graph showing processed signals, the images and graph illustrating example data analysis performed using embodiment devices and methods.

FIG. 1E illustrates an example analysis process that was used to extract final PSM signals from raw data collected by the camera 111 in the experimental device of FIG. 1D. The data processing illustrated in FIG. 1E was performed by a computer processor to extract a final PSM signal 156 from raw camera images 115. Raw camera frames 115 of 100×100 pixels showing speckle patterns 114 resulting from probe light 108 reflected from the target specimen 112 were typically collected at 50 Hz frame rate. The two-dimensional images were collected over time t as the speckle pattern changed in response to pump light amplitude modulation. The processor then performed an FFT on the values for each pixel in the images 115. The FFT values for each pixel were then averaged over all pixels to obtain the averaged FFT magnitude 156 illustrated in FIG. 1E on the graph 155. This analysis process is further described hereinafter in the description of FIGS. 8A-8B.

In the FFT spectrum 156 illustrated in FIG. 1E, a peak occurs at a single frequency, namely the 22 Hz modulation frequency of the pump light source used for experimental purposes. However, modulation frequency can be varied over time, as illustrated, for example, in FIGS. 5E, 6, and 10A. In these cases, a peak in FFT magnitude can occur at a different frequency at different times. The different peak sizes at different modulation frequencies can then be analyzed as a probe of thermal diffusivity of the target specimen, as illustrated in FIG. 5D, for example.

Figure 4B:
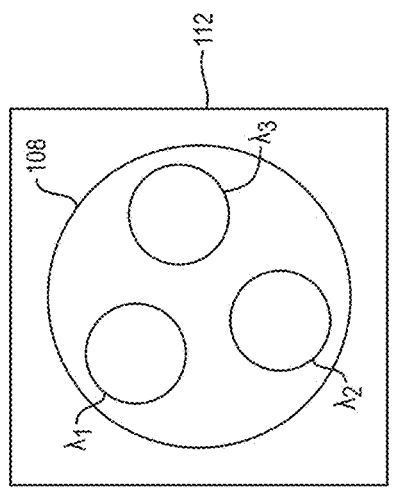
FIG. 4B illustrates the multiple wavelengths of pump light shown in FIG. 4A overlapping with probe light but not overlapping with each other.
Figure 4C:
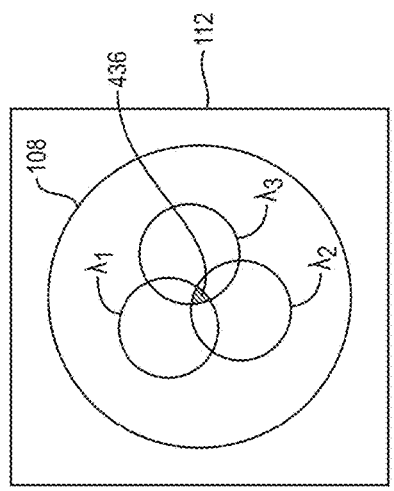
FIG. 4C illustrates the multiple wavelengths of pump light shown in FIG. 4A overlapping with the probe light and with each other.
Figure 4A:
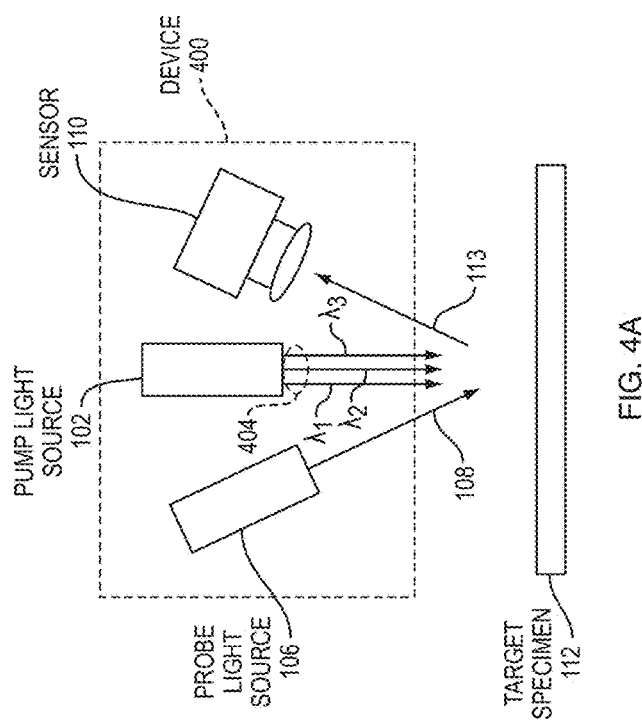
FIG. 4A illustrates an embodiment device with a pump light source configured to output multiple wavelengths of pump light simultaneously.
Figure 4D:
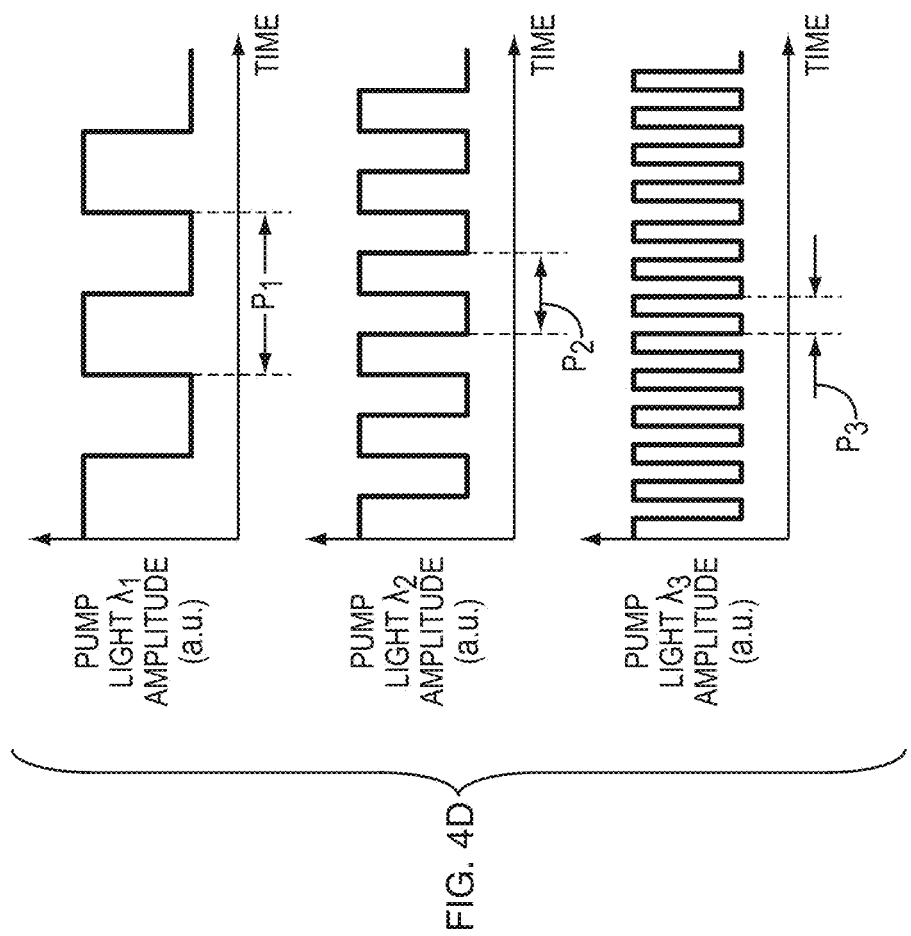
FIG. 4D illustrates different pump light amplitude modulation frequencies for the different pump light wavelengths illustrated in FIG. 4A.

Furthermore, in yet other embodiments, multiple modulation frequencies can be used simultaneously, as illustrated in FIGS. 4C and 4D, for example. In these cases, multiple peaks can occur in the same FFT magnitude spectrum at distinct frequencies, instead of the single peak 156 illustrated in FIG. 1E. Similarly, in these cases, the difference in peak height can yield information about frequency behavior and thermal diffusivity of the target specimen. In cases in which multiple modulation frequencies correspond to different pump laser wavelengths, as illustrated in FIGS. 4A and 4B, multiple peaks can occur in the FFT magnitude spectrum, providing spectral absorption information for the target sample.

Figure 1F:
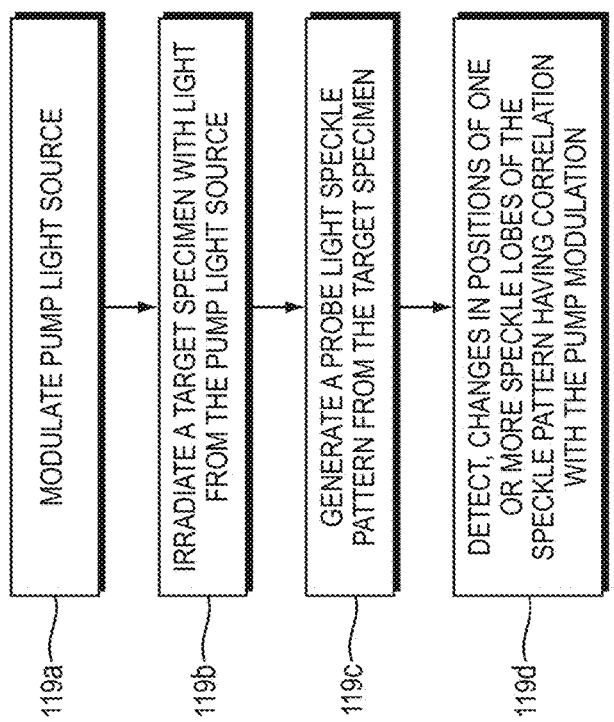
FIG. 1F is a flow diagram illustrating a method according to an embodiment.

FIG. 1F is a flow diagram illustrating an embodiment method that can be performed using the device 100 illustrated in FIG. 1A, for example. At 119a, the pump light source 106 is modulated to produce modulated pump light, as illustrated by the specific case of amplitude modulation 120 in FIG. 1A, for example. At 119b, a target specimen such as the specimen 112 is irradiated with the modulated light from the pump light source. At 119c, a probe light speckle pattern such as the speckle pattern 114 illustrated in FIG. 114 is generated from the target specimen. At 119d, changes in positions of one or more speckle lobes of the speckle pattern having correlation with the pump modulation are detected.

Figure 1G:
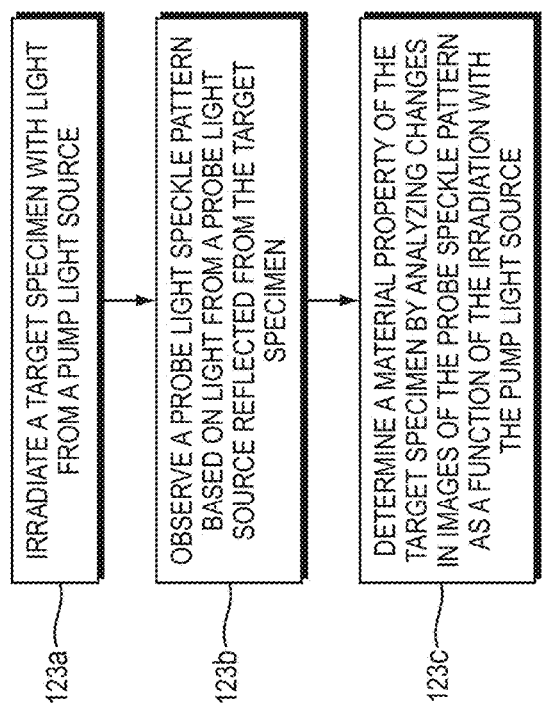
FIG. 1G is a flow diagram illustrating a method according to an embodiment.

FIG. 1G is a flow diagram illustrating an embodiment method of remote detection. The method illustrated in FIG. 1G can also be performed using the device illustrated in FIG. 1A, for example. At 123a, a target specimen is irradiated with light from a pump light source. At 123b, a probe speckle pattern is observed based on light from a probe light source, with the probe light reflected from the target specimen. At 123c, a material property of the target specimen is determined by analyzing changes in images of the probe speckle pattern as a function of the irradiation with the pump light source.

Material properties that can affect pump light absorption by the target specimen can include, for example, chemical composition, absorption spectrum, a range of thermal diffusivities, or a material class such as metal or plastic. For example, in one embodiment, a target specimen can be irradiated with an amplitude-modulated pump light source at a particular pump wavelength. The target specimen is also co-illuminated with light from a probe light source. Changes in positions of one or more speckle lobes of the speckle pattern that occur at the modulation frequency can be detected and differentiated from changes that may occur for other reasons such as deflection of light due to air disturbances of target thermal drift. The modulation period can be shorter than a time scale of blurring of the speckle pattern in some cases. The intensity of the changes in positions can then be quantified, for example, using the previously described FFT algorithm. The pump light source can be tuned to one or more other wavelengths, and the same steps can be repeated at each chosen wavelength in a wavelength range of interest. The quantified intensities of the changes in positions at various wavelengths can be correlated to the absorption spectrum of the target specimen.

Figure 6:
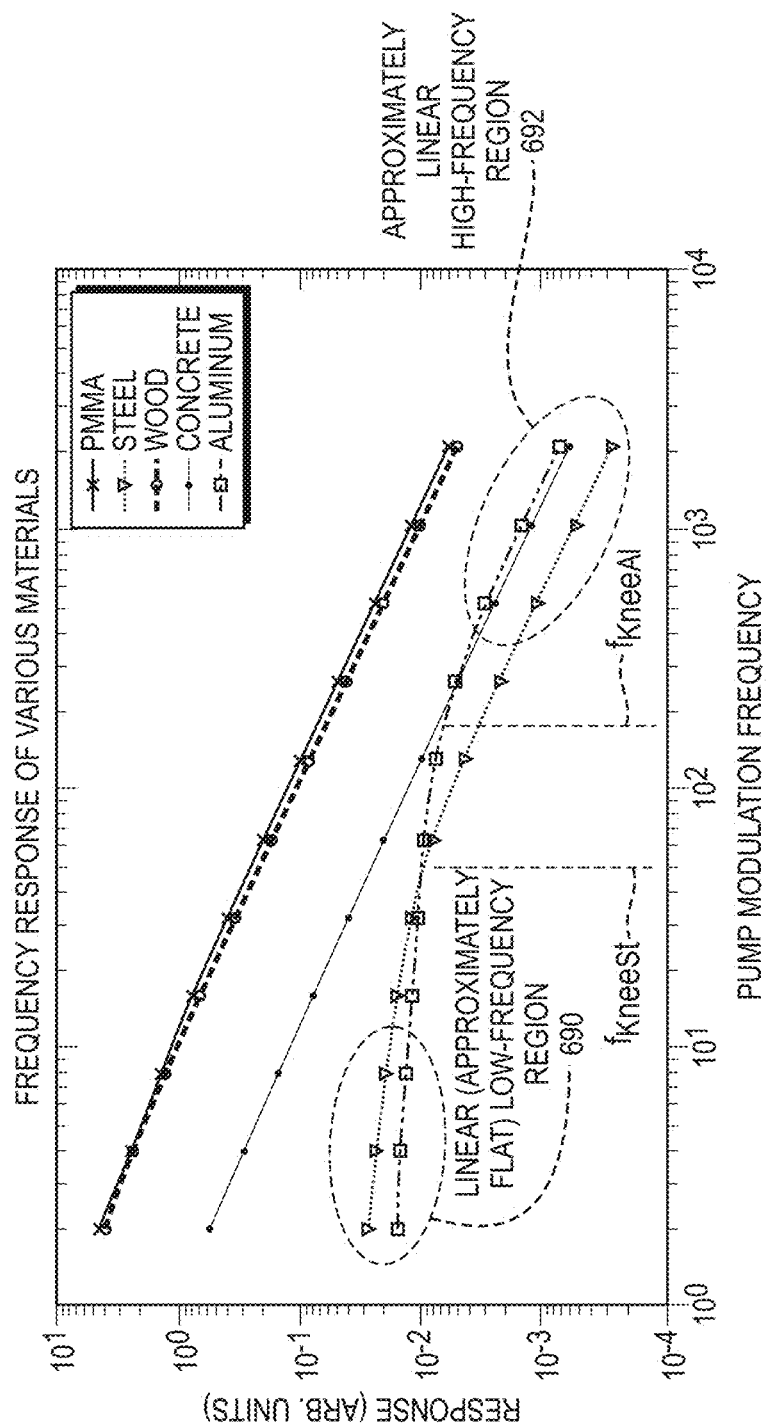
FIG. 6 is a graph illustrating calculated frequency responses that can be exploited by embodiment devices and methods to differentiate between various classes of materials or determine a material property.

In another embodiment, a material class of the target material can be determined as follows. A sample can be irradiated with an amplitude-modulated pump laser at a particular pump wavelength. Changes in positions of one or more speckle lobes of the speckle pattern can then be detected at the modulation frequency, and the modulation period can be on a time scale shorter than a time scale of blurring of the speckle pattern due to thermal input to the target or due to environmental changes, for example. The intensity of the changes in positions is then quantified, for example, using the previously described FFT algorithm. The amplitude modulation frequency can then be changed, and the irradiation and quantification can be repeated at each chosen modulation frequency. Typical modulation frequencies of interest can range from 10 Hz-1000 Hz, for example. The intensities thus computed as a function of pump modulation frequency will generally be different for different classes of materials and can, thus, be used to distinguish one target material from another. Example calculations showing how signal intensities are expected to scale for different materials are illustrated in FIG. 6. In other embodiments, for example, the pump light source need not be modulated periodically, but only turned on and then off at particular times. A material class such as metal versus wood, can then be determined. Such an embodiment that does not require modulation is illustrated, for example, in FIGS. 11A-11E. In such embodiments, a correlator such as the correlator 117 in FIG. 1A or another processor can determine the material property by analyzing changes in the images of the probe speckle pattern as a function of the irradiation with the pump light source.

Figure 2:
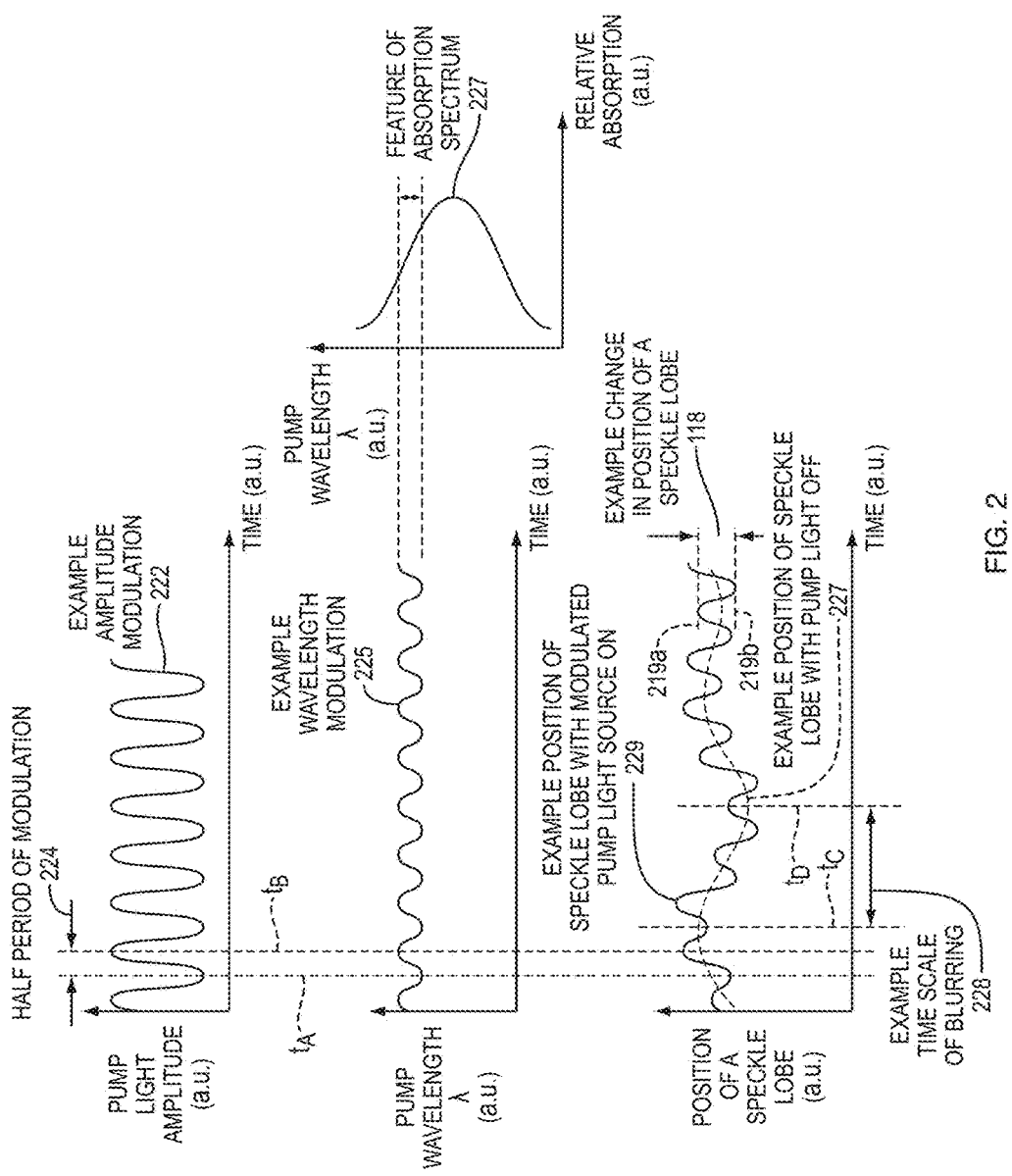
FIG. 2 illustrates pump light amplitude and wavelength modulation and corresponding changes in speckle lobe position.

FIG. 2 illustrates two different types of pump light source modulation. For example, the pump light amplitude 222 is modulated in time with sine wave modulation having a non-zero offset. One example timescale for modulation of the pump light source is the time difference between minimum in amplitude and time $t_A$ and a maximum in amplitude at time $t_B$ (a half modulation cycle period 224), but other example timescales for modulation can include a full modulation period, several full modulations periods, or a fraction of the half period 224 in which pump light amplitude changes such that the periodic effect in the speckle lobe position 229 can be measured.

FIG. 2 also shows an example wavelength modulation 225, in which the pump wavelength λ is modulated. In this example wavelength modulation 225, the modulation period (twice the half-cycle period 224) is the same as for the amplitude modulation 222 for convenience of illustration. An example absorption feature 227 of an absorption spectrum of a target specimen is also illustrated. As the pump wavelength is modulated over time, the wavelength is closer to a peak of the absorption feature 227 or further away from the peak, resulting in varying absorption over time. Note that, in the example where the pump wavelength is modulated and the pump laser amplitude remains the same, the speckle modulation signal will be proportional to the derivative of the absorption versus wavelength. This is in contrast to the case of amplitude modulation, in which the speckle modulation signal will be proportional to the absorption.

Thus, in instances in which absorption wavelengths of potential targets are known, pump wavelength can be modulated near wavelength regions on absorption features of potential targets to look for correlated variation in speckle lobes of a speckle pattern. A tunable laser can be used, for example, for pump wavelength modulation over time. Furthermore, in other cases, the modulation of the wavelength may cover a larger portion of the absorption feature 227, or even the entire absorption feature 227. Nevertheless, in cases where it is desirable to distinguish between multiple materials in the target specimen with closely spaced absorption features, it is preferable to modulate the pump wavelength as indicated in FIG. 2 over a small portion of the absorption feature 227.

FIG. 2 also includes a graph illustrating an example position 229 of a speckle lobe in a speckle pattern over time when modulated with either a pump light amplitude modulation or a pump wavelength modulation, respectively. As illustrated in FIG. 2D, an example change in position 118 of the speckle lobe is correlated with the pump modulation, whether modulation of light amplitude or modulation of wavelength of the pump light source. Note that, in the case of amplitude modulation, the speckle lobe position changes in proportion to absorption at the pump wavelength, whereas for wavelength modulation, the speckle lobe change is proportional to the derivative of the absorption spectrum. Thus, the example position 229 of the speckle lobe with the modulated pump light source on is correlated with the modulation period and frequency of the pump light source, and this correlation can be discerned by using lock-in amplifier or a processor running at FFT, for example.

However, even with the pump light source off, there can be some variation in position of a speckle lobe due to transient thermal, vibrational, or refractive changes. For example, there can be a thermal transient in the target specimen 112 illustrated in FIG. 1A. Furthermore, atmospheric conditions can cause some deflection of light irradiating the target 112 from the probe light source, and light traveling from the target 112 toward the sensor 110 can similarly be impacted by atmospheric conditions. Thus, even with the pump light off, there can be an example variation 227 in position of the speckle lobe over time. Furthermore, as the pump light is modulated, the target specimen can expand or contract or otherwise vary as absorption of the pump light occurs or as thermal diffusivity or convection cause thermal relaxation. The example timescale 224 for modulation of the pump light source can be shorter than an example timescale 228 of blurring of the speckle pattern, such that variations in the position of the speckle lobe caused by modulation of the pump light source can be distinguished. The example timescale 228 for blurring is the difference in time between a local maximum in speckle lobe position at time $t_C$ and a local minimum in speckle lobe position at time $t_D$. This blurring can result from environmental deflection of the probe beam due to air currents, or longer-term heating caused by turning the pump light source, or to temperature transients in the target that are unrelated to the pump light source, for example.

These timescales illustrated in FIG. 2 exemplify a difference between the modulation transfer method described herein and the existing photothermal speckle imaging based on measuring a contrast change alone. Methods based on measuring a contrast change alone can work only if the only source of speckle motion is the photothermal excitation. In many applications, for example, measuring a material on a vibrating surface, such as on a car door with engine running, the previously reported speckle contrast imaging method would produce obfuscating results due to the difficulty in separating photothermally induced speckle contrast changes with vibration induced speckle contrast changes. In contrast, the modulation transfer technique described herein can facilitate excitation of a target at a particular modulation frequency, and measurement of the resulting speckle modulation only at that frequency, thereby being unaffected by randomly distributed vibrations occurring at frequencies other than the pump modulation.

The sensor 110 in FIG. 1A or sensor camera 111 in FIG. 1D can be configured to detect changes in positions of one or more speckle lobes of the speckle pattern, which are correlated with the pump modulation, on a timescale shorter than a timescale of blurring of the speckle pattern. The example change in position 118 illustrated in FIG. 1A is representative of the difference between a local peak 219a of a position of the speckle lobe and a local valley 219b of the position. Thus the example change in position or amplitude 118 can be referred to as a peak-to-valley (PTV) response.

Furthermore, while not illustrated in FIG. 2, some target specimens can have absorption that is sensitive to light polarization. Light from a pump light source can be modulated in polarization, and the sensor can be configured to detect the changes in positions of the speckle lobes as a function of the light polarization modulation, similar to the case of the correlation illustrated in FIG. 2 between the example change 118 in position of the speckle lobe correlated with pump light amplitude modulation or pump wavelength modulation.

Figure 3A:
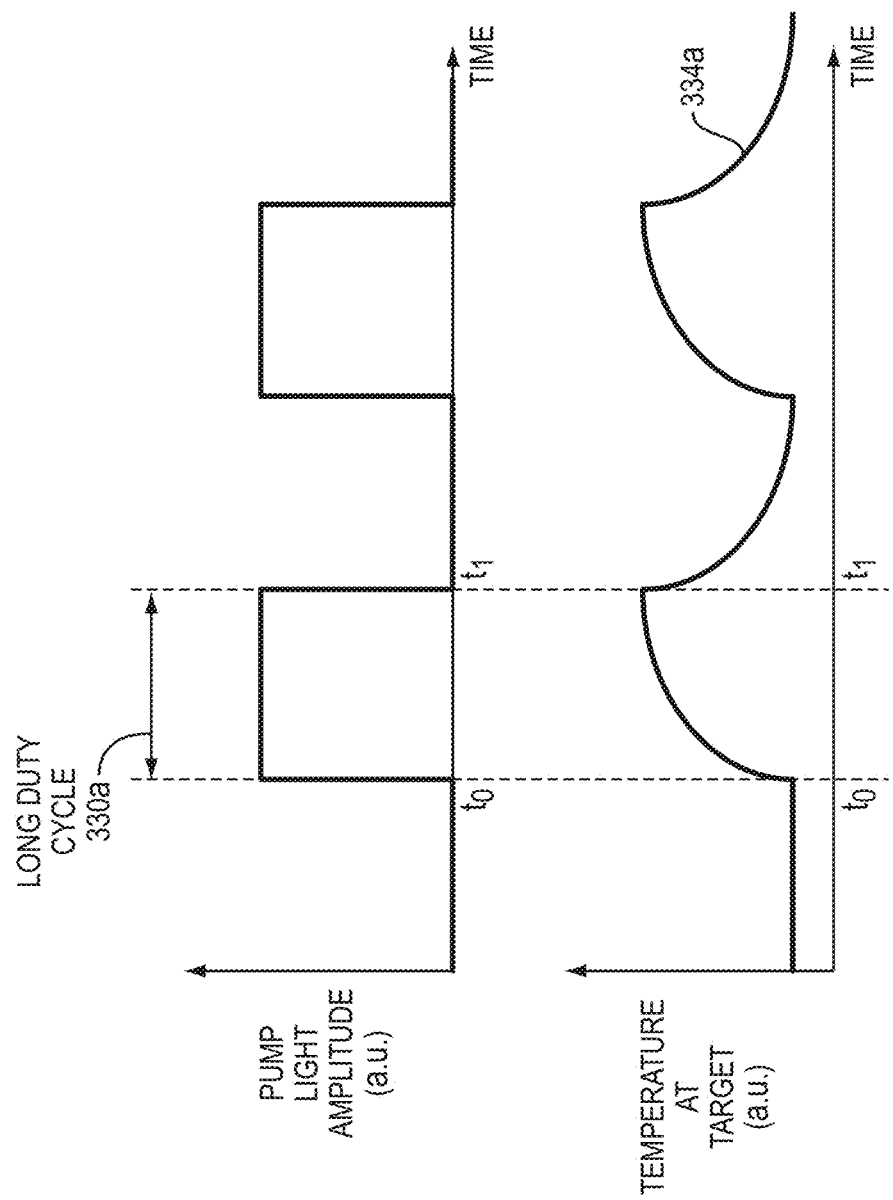
FIG. 3A illustrates pump light duty cycles that are long with respect to a thermal diffusion time of a target specimen and a timeframe of blurring of a speckle pattern.

FIGS. 3A-3B illustrate pump light modulation duty cycles that are long and short, respectively, in comparison with timeframes for thermal diffusion of a target. "Duty cycle," as used herein, denotes a time period during which the pump light source is irradiating the target specimen. In particular, FIG. 3A illustrates a relatively long duty cycle 330a (the time between the start of a pulse at $t_0$ and the end of the pulse at $t_1$) for pump light amplitude modulation. FIG. 3A also illustrates a corresponding temperature curve 334a for a given position at the surface of the target specimen during the duty cycles of the pump light. This temperature curve 334a is directly related to thermal diffusion in the material of the target specimen. The duty cycle 330a is long in comparison with the thermal diffusion time of the target because overall temperature rise in the target following the start of the duty cycle at $t_0$ continues during most of the duty cycle. Where the duty cycle is long in comparison with the thermal diffusion time, as in the duty cycle 330a, temperature at a given position of the target specimen depends both on thermal diffusion and on any heating caused by the pump light during the duty cycle of the pump light. In this case, the temperature will continue to rise, so long as the pump laser is on, until a steady state temperature is reached. In some embodiments, a long duty cycle can be on the order of 1 second, for example, as further illustrated in FIG. 11B. However, whether a duty cycle is long or short is determined, in part, by the thermal diffusion time of the target specimen material, which can vary significantly for different materials.

FIG. 3B, in contrast to FIG. 3A, illustrates a short duty cycle 330$b$ for pump light pulses. In particular, FIG. 3B illustrates that in some embodiments, a duty cycle of light amplitude modulation of the pump light source can be small in comparison with a thermal diffusion time of the target specimen. A short duty cycle time period can be very short, such as in cases where the pump light source is a pulsed laser having a pulse width in the range of milliseconds, microseconds, nanoseconds, or femtoseconds, for example. However, in other embodiments, a short duty cycle can be on the order of fractions of a second, such as tenths or hundredths of a second, for example. Short duty cycles on the order of tenths or hundredths of seconds can be provided by optical choppers that block a pump laser beam at various time intervals, or by electronic modulation or other types of modulation, for example. FIG. 3B also illustrates an example temperature profile 334$b$ at a given irradiated position of the target specimen 112 in response to the pump light excitation of short duty cycle 330$b$, in which all the energy is deposited into the target in a very short time scale relative to thermal diffusion. In this case of short duty cycles, the temperature first rises very rapidly starting at the beginning $t_0$ of the pulse in response to the short pulse at the given position and then relaxes in temperature over time starting at the end $t_1$ of the pulse. The temperature relaxation extends over a time period longer than the short-duty-cycle pulse, and the rate is determined by thermal diffusion time within the target specimen. In cases of short duty cycles, as in FIG. 3B, there can also be a long-term temperature change as modulated pump light is turned on. This longer-term effect is not illustrated in FIG. 3B, but it is illustrated in FIG. 10A.

FIGS. 4A-4D illustrate how multiple wavelengths of pump light can be used in some embodiments. In particular, the pump light source can be configured to irradiate the target specimen with a plurality of wavelengths of pump light simultaneously, and the plurality of wavelengths can be incident at the target specimen at different locations of the target specimen or overlapping. In the device 400 illustrated in FIG. 4A, the pump light source 102 illustrated in FIG. 1A is replaced by a pump light source 402 that outputs three wavelengths, $\lambda_1$, $\lambda_2$, and $\lambda_3$. The multiple wavelengths can be useful for determining part of an absorption spectrum of a target specimen such as a chemical, for example. In the device 400, the pump light source 402 outputs the wavelengths $\lambda_1$, $\lambda_2$, and $\lambda_3$ simultaneously. In other embodiments not shown in FIGS. 4A-4D, the pump light source can be a tunable laser, for example, in which the various wavelengths are used in succession by tuning the laser, and the light 404 is always directed to the same position of the target specimen. A pump light source can include multiple light sources configured to output the various wavelengths. As used herein, the term "pump light source" refers to any pump light source or combination of sources that are configured to output one or more wavelengths of pump light.

FIG. 4B shows a region 108 of the target 112 in which the various wavelengths $\lambda_1$, $\lambda_2$, and $\lambda_3$ are incident. The wavelengths are incident at different locations of the region 108, and modulation of the individual wavelengths can occur at the same or different frequencies. Where the sensor 110 is a camera with a pixel array, for example, the individual subregions illuminated by the various wavelengths can be independently monitored and analyzed for movement in speckle positions.

FIG. 4C, in contrast to FIG. 4B, illustrates how the various wavelengths can be at least partially overlapping with an overlap region 436. Furthermore, in other cases not shown, the areas in which the various wavelengths are incident may be almost entirely overlapping. Where these wavelengths are simultaneously incident at the region 108 of the target, it can be useful to modulate the different wavelengths of light at different modulation frequencies as illustrated in FIG. 4D.

FIG. 4D illustrates how the various wavelengths $\lambda_1$, $\lambda_2$, and $\lambda_3$ can be modulated at different frequencies to distinguish the effect of each wavelength even when the wavelength overlap, as in FIG. 4C. Pump light amplitude of the wavelength $\lambda_1$ is modulated with a modulation period $P_1$, with the modulation frequency being $1/P_1$. In contrast, pump light amplitudes for the wavelengths $\lambda_2$ and $\lambda_3$ have periods $P_2$ and $P_3$, respectively, and corresponding modulation frequencies $1/P_2$ and $1/P_3$, respectively. Thus, even in the case illustrated in FIG. 4C where the wavelengths are simultaneously incident and overlapping, a single signal from the sensor 110 including the effects of all modulation frequencies and wavelengths can be analyzed using correlator such as a processor running an FFT, for example, or a lock-in amplifier, for example. The response of the speckle pattern 114 to each individual wavelength of pump light can thus be distinguished. Thus, using embodiments with multiple wavelengths of pump light, for example, it is possible to determine an absorption spectrum of a target specimen more rapidly and efficiently. These principles are illustrated further hereinafter.

FIGS. 5A-5D illustrate two different ways in which embodiments of the invention can be used, namely identification of, or differentiation between, one or more target materials in a target specimen based on (i) absorption spectrum or (ii) thermal diffusivity. Embodiments can have applications in defense, counterfeit detection, manufacturing quality monitoring, environmental protection, and many others.

Figure 5A:
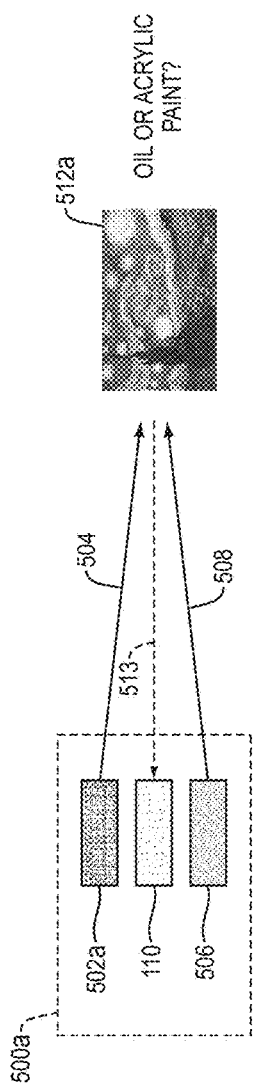
FIG. 5A illustrates an embodiment device configured to differentiate various chemical target species based on absorption spectrum.
Figure 5B:
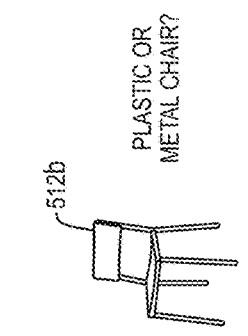
FIG. 5B illustrates example speckle modulation amplitudes that can be used to distinguish between different target materials, using the device of FIG. 5A, on the basis of absorption spectrum.

FIGS. 5A-5B illustrate the case of absorption spectrum measurements used to distinguish between different chemicals or classes of chemical materials. For example, a device 500$a$ in FIG. 5A is configured to distinguish different chemical species, such as a determination of whether the painting 512$a$ includes oil or acrylic paint. In the device 500$a$, an infrared pump light source 502$a$ is used, and a probe light source 506 is a green laser. A pump light source 502$a$ is a tunable infrared laser and can be used to scan wavelength over distinguishing features in absorption spectra for chemicals of interest. This principle is illustrated further in FIG. 5B, which shows a feature A in the speckle modulation amplitude obtained for a first chemical species and a feature B in the speckle modulation amplitude obtained for a second chemical species. Because the speckle modulation amplitude varies roughly proportionally to the absorption spectrum, the first and second chemical species can thus be distinguished and detected on the basis of the remotely applied light wavelengths using the tunable pump light source 502$a$. In particular, when the target is irradiated by pump light, absorption, surface deformation, and speckle pattern modulation amplitude are approximately proportional to each other. Thus, monitoring speckle modulation amplitude as a function of pump laser wavelength is a sensitive way to distinguish one material from another on the basis of absorption spectrum.

Figure 5C:
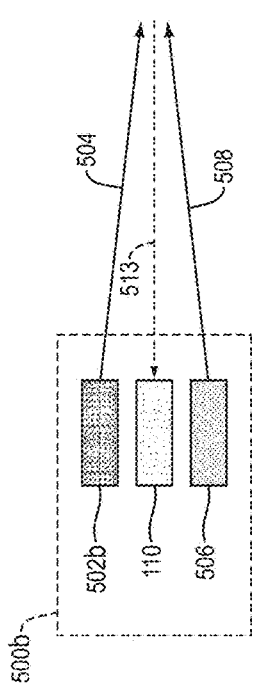
FIG. 5C illustrates an example device configured to remotely distinguish between classes of target materials on the basis of thermal diffusivity.
Figure 5D:
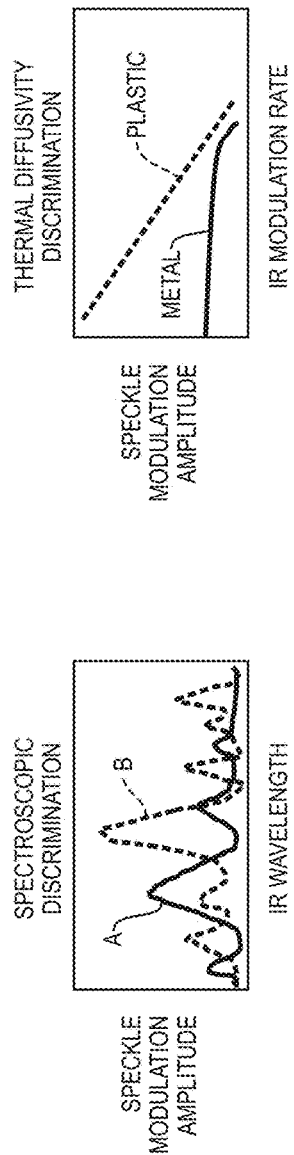
FIG. 5D illustrates example data that can be used to differentiate target materials, using the device of FIG. 5C, based on variation of speckle data with frequency due to thermal diffusivity.

FIG. 5C, in contrast to FIG. 5A, illustrates a device 500b with a pump laser 502b operating at a fixed wavelength. The device 500b is configured to determine whether the chair target 512b is metal or plastic on the basis of infrared (IR) pump laser modulation rate (modulation frequency). This frequency-based approach can be effective even where, for example, metal and plastic chairs have identical coatings.

As illustrated in FIG. 5D, at lower pump modulation frequencies, the speckle modulation amplitude (see, e.g., example change 118 in position of speckle lobe correlated with pump modulation in FIG. 2) is relatively high. The speckle modulation amplitude of plastic is much higher than that of metal for low frequencies due to lower thermal diffusivity of plastic. However, as pump modulation frequency increases, the speckle modulation amplitude of the chair 512b decreases rapidly if it is made of plastic, while the speckle modulation amplitude of the chair 512b remains relatively unchanged over a wider range of modulation frequencies before it finally drops off at higher pump modulation frequencies if it is made of metal. This difference in speckle modulation amplitude over a range of frequencies can be exploited to distinguish between the different materials or classes of materials such as plastic 512 and metal 512 on the basis of thermal diffusivity.

Thermal diffusivity-based differentiation can be particularly helpful in the case of two materials with the same surface color or coating. This can be used, for example, in differentiating counterfeit materials that are made to appear like real ones. For example, it may be desirable to distinguish between a plastic chair and a metal chair, each of which looks the same because the surface paint is the same. These materials can be distinguished using the device and technique of FIG. 5C-5D with the realization that, even if plastic and metal chairs 512b are painted the same color, the rate of heat dissipation from the paint will be very different depending on the underlying material. Thus, by examining the amplitude of the speckle response to a varying IR modulation frequency as in FIG. 5D, the underlying materials can be distinguished without contact, facilitating remote sensing.

Figure 5E:
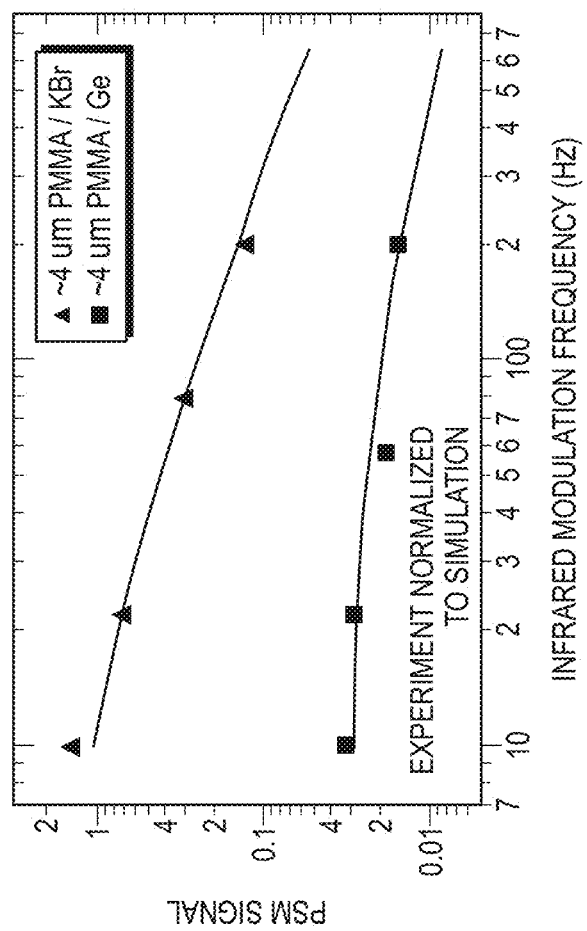
FIG. 5E is a graph illustrating how example germanium (Ge) and potassium bromide (KBr) substrates can be distinguished using frequency-based thermal diffusivity discrimination as illustrated in FIG. 5D.

FIG. 5E is graph showing experimental demonstration of the frequency dependence principle illustrated in FIG. 5D. In the experiments illustrated in FIG. 5E, 4 μm thick Poly(methyl methacrylate) (PMMA) layers were applied to germanium (Ge) and potassium bromide (KBr) substrates. Using a QCL pump light laser source having wavelength 7.85 μm (1274 cm$^{-1}$), an average pump light intensity of 1 W/cm$^2$ was applied to the two PMMA layers. A sensor camera collected images at 500 frames per second with an exposure time of 0.2 milliseconds per frame. The pump light modulation frequency was tuned from 10 Hz through 200 Hz, and the photothermal speckle modulation signal was analyzed for each frequency, all at the same pump wavelength. Because the Ge substrate is more conductive (and therefore has a higher thermal diffusivity) than KBr, the signal falls off slower with frequency for Ge. Also, since the coefficient of thermal expansion is larger for KBr than for Ge, the overall signal strength is higher for KBr compared to Ge. The triangles and squares are the measured data PSM signals, while the curves are calculations using the finite element program Nastran.

Although the surface materials for the two curves in FIG. 5E are the same (PMMA), the difference between the functional forms of the PSM signals as a function of IR pump light modulation frequency allows the two underlying substrates to be distinguished from each other due to their differing thermal diffusivities. Thus, a useful feature of embodiment methods and devices is the ability to distinguish between different sub-surface materials of respective objects, even where surface layers or surface finishes of the respective objects are identical.

FIG. 6 is a graph illustrating calculated frequency responses for PMMA, steel, wood, concrete, and aluminum. These differing frequency responses can be exploited using embodiment devices and methods to differentiate between various classes of materials. As in FIGS. 5D-5E, the strong frequency dependence (at low frequencies) of the low thermal diffusivity materials, such as PMMA and wood, is in contrast to the relatively small dependence of signal with frequency for high conductivity materials, such as aluminum. Note that the magnitude of the response depends on a number of material properties, including CTE, specific heat, density, and thermal conductivity, but these properties determine the scale of the response and not the shape of the curve.

The calculated curves illustrated in FIG. 6 are characterized, respectively, by a relatively linear low-frequency region 690 having smaller absolute slope and a relatively linear high-frequency region 692 having greater absolute slope, and the two regions of each curve are joined by a "knee" area where most of the slope change occurs. These knee areas are particularly visible for the steel and aluminum response curves, which have relatively high thermal diffusivities. Lower diffusivity materials such as PMMA, wood, or concrete would still produce a flat region but at frequencies lower than shown on this plot.

In addition to the calculated response curves illustrated in FIG. 6, experiments using embodiment devices and methods have been performed, and good fidelity to the calculated curves has been obtained. As expected, aluminum (thermal diffusivity of 70 mm$^2$/s) has a nearly flat response at low frequencies, while PMMA (thermal diffusivity of 0.1 mm$^2$/s shows a 1/frequency dependence (inverse frequency relationship) starting around 10 Hz.

The response (PSM signal) curves shown in FIG. 6 depend on a number of material properties, including CTE, specific heat, density, and thermal conductivity. Because the CTE affects only the scale of the response, the shape of the frequency response curves of FIG. 6 is primarily dependent on the specific heat, density, and thermal conductivity. These three properties are commonly combined into thermal diffusivity, which has dimensions of length squared divided by time. The thermal diffusivity is inversely proportional to the apparent thermal time constant, and the apparent time constant is responsible for the shape of the frequency response curve. This suggests a quantitative method for measuring thermal diffusivity. Specifically, it is proposed that the transition (knee) between the flat and sloped portions of the curve occurs at a frequency that is proportional to the thermal diffusivity. The dimensions of diffusivity suggest that geometric factors such as the spot size, absorption depth, or thickness of the material may also influence the shape of the curve, perhaps requiring some calibration to obtain an absolute measure of thermal diffusivity.

Various material properties can be determined or estimated using embodiment devices and methods. For example, as shown in FIG. 5B, IR absorption peaks, features, wavelengths, and spectra can be obtained. Moreover, material properties can be estimated from modulation frequency variation measurements similar to those illustrated in FIG. 5D and calculations such as those shown in FIG. 6. For example, thermal diffusivity can be determined or estimated as described hereinafter.

In FIG. 6, a center of the knee area for steel, $f_{kneeSt}$ (around 40 Hz), and center of the knee area for aluminum, $f_{kneeAl}$ (around 100 Hz) are shown. Also shown is a hypothetical center of a knee $f_{kneeUn}$ for a hypothetical unknown material. Since the location of the knee, in frequency, is strongly correlated with overall thermal diffusivity, a measurement of the knee location for the unknown, $f_{kneeUn}$, can be used to obtain an estimate for a thermal diffusivity $\alpha_{Un}$ of the unknown material. For example, a linear interpolation can be performed to obtain based on the equation $\alpha_{Un}=\alpha_{St}+ (\alpha_{Al}-\alpha_{St})(f_{kneeUn}-f_{kneeSt})/(f_{kneeAl}-f_{kneeSt})$, where $\alpha_{St}$ and $\alpha_{Al}$ are the known thermal diffusivities of steel and aluminum, respectively. In an embodiment device, such calculation can be performed by the correlator 117 illustrated in FIG. 1A based on measurements similar to the calculated values illustrated in FIG. 6 or the measured values illustrated in FIG. 5E, for example. The knee, or inflexion point, for PMMA is not indicated in FIG. 6 but is clearly at a much lower frequency (estimated to be less than 2 Hz). Thus, if a scan of modulation frequencies in the range of 30-110 Hz indicates a presence of a knee for an unknown material surface, this indication can be used to conclude that the material is likely a metal with thermal diffusivity in the range of steel and aluminum, and not a plastic or other material with a thermal diffusivity in the range of PMMA, for example. Therefore, in this manner, even where a specific unknown material cannot be identified due to measurement precision of a given measurement, for example, these measurements can still be used to distinguish between various classes of unknown materials. For example, as described hereinabove, the location of a knee (inflexion point) can indicate that a material is likely a plastic or likely a metal.

Nonlinear interpolation or even linear or nonlinear extrapolation can be used, using techniques known to those skilled in the art of data analysis, if device calibration and further study indicate that linear interpolation does not provide the most accurate determination of thermal diffusivity for a given set of known and potential unknown materials. Nevertheless, linear interpolation as described above is one way to determine an estimated thermal diffusivity of an unknown material. Moreover, in view of the devices and methods described, it will be understood readily that, given an estimated thermal diffusivity for the unknown material, the unknown material may be identified. A table of known materials with known thermal diffusivities, for example, may be used to determine the unknown material based on the estimated thermal diffusivity determined for the unknown material. Furthermore, even where measurement error bars do not permit determination of an exact unknown material, an unknown material may be determined to be within a class of materials, such as plastic, metal, etc., because these classes typically have very different ranges of thermal diffusivities.

Figure 7A:
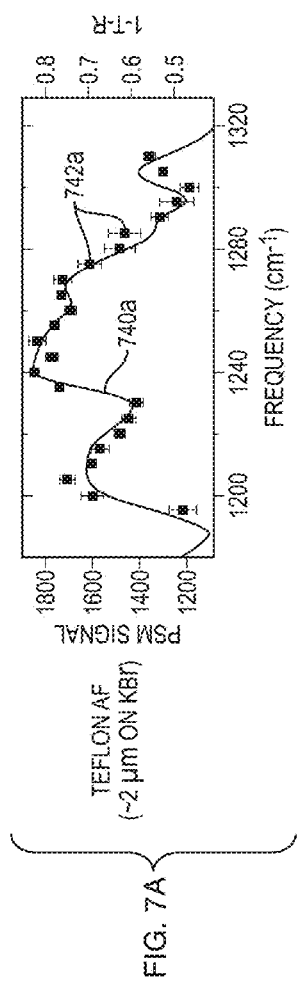
FIGS. 7A-7C are graphs illustrating photothermal speckle modulation (PSM) spectra of various thin films on transparent KBr substrates, the spectra obtained using an embodiment device.
Figure 7B:
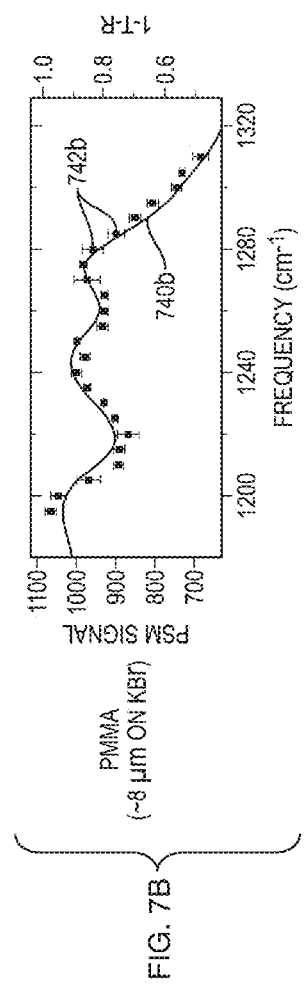
Figure 7C:
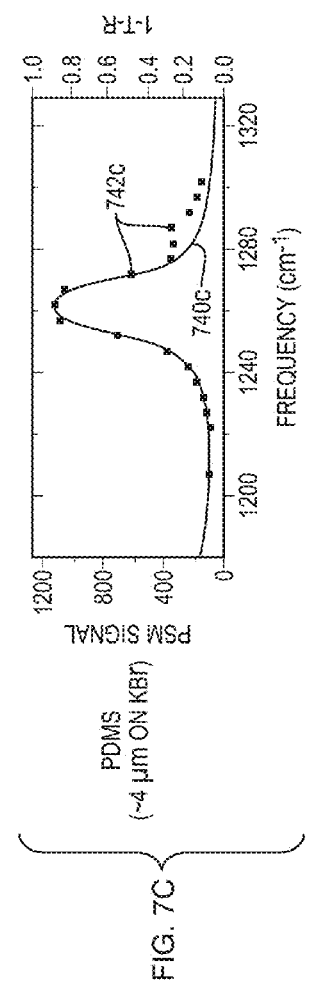

FIGS. 7A-7C are graphs illustrating PSM spectra of various thin films obtained using an embodiment device. FIG. 7A shows PSM signal and measured absorption as a function of wavenumber for a thin film of Teflon (2 μm thick) on a KBr substrate. FIG. 7B shows similar data for a PMMA thin film (8 μm thick) on KBr substrate, while FIG. 7C illustrates similar data for a polydimethylsiloxane (PDMS) thin film (4 μm thick) on a KBr substrate. In each of the cases illustrated in FIG. 7A-7C, Teflon, PMMA, and PDMS were chosen due to their strong absorption spectra in the wavelength region covered by the particular pump light source used for these measurements, which in this case was a pulsed, wavelength-tunable quantum cascade (QC) laser.

The respective, known absorption curves 740a-c were measured by using Fourier transform infrared (FTIR) spectroscopy to measure transmission (T) and reflectance (R) and then deducing absorbance (A) using the equation A=I-T-R. The PSM signal data seven 428a-c were measured in accordance with the technique described hereinafter. All films were formed by standard spin coating techniques.

The PSM signal data 742a-c were measured as follows. The pump beam from a pulsed wavelength-tunable quantum cascade laser (1 MHz pulses, 10% duty cycle, Daylight Solutions laser) was focused to a 0.6 mm FWHM spot on the surface of the sample using a 50 cm piano-convex lens. A probe beam from a continuous-wave (cw) 532 nm solid state laser was directed at the surface with a 2 mm FWHM spot and was aligned to be concentric with the IR spot. The pump laser was amplitude modulated at 22 Hz with a 50% duty cycle using a function generator. A fraction of the scattered probe light was collected with a high-speed camera (Andor Zyla 5.5) equipped with telephoto lens (f=160 mm) set to global shutter mode and operating at a frame rate of 50 Hz. For each IR wavelength, a series of 1000 consecutive frames were recorded, each frame consisting of 124×124 pixels.

The PSM signal at each pump wavelength was extracted from the captured frames using a two-step algorithm: First, an FFT was applied on the intensity value of each individual pixel, where the frame number (1 to 1000) represents the time coordinate of that pixel's intensity value. Applying the FFT algorithm to each pixel results in an FFT spectrum for that pixel. Second, the FFT spectrum calculated for each pixel is averaged over all of the pixels to yield the average FFT spectrum, as illustrated in FIG. 1E and in FIG. 8A. The PSM signal at each wavelength can be extracted from this spectrum by the following equation: PSM signal= $\sqrt{FFTamplitude^2-Noisefloor^2}$. The PSM signal for each pump wavelength was plotted against the FTIR-measured absorption (1-T-R) for the three different materials. As illustrated in FIGS. 7A-7C for each respective material, excellent matches were observed between the PSM signals and the respective materials' absorption spectra. FFTs were used to deduce PSM signals, as illustrated further in FIGS. 8A-B. Thus, FIGS. 7A-C illustrate the effectiveness of embodiment methods and devices in measuring absorption spectra of example thin films based on the PSM.

In the cases illustrated in FIGS. 7A-7C, data were averaged over all pixels. However, in other embodiments, individual pixels, displacement of individual speckle lobes, or the velocity of a given speckle lobe could be analyzed to obtain similar results.

Figure 7D:
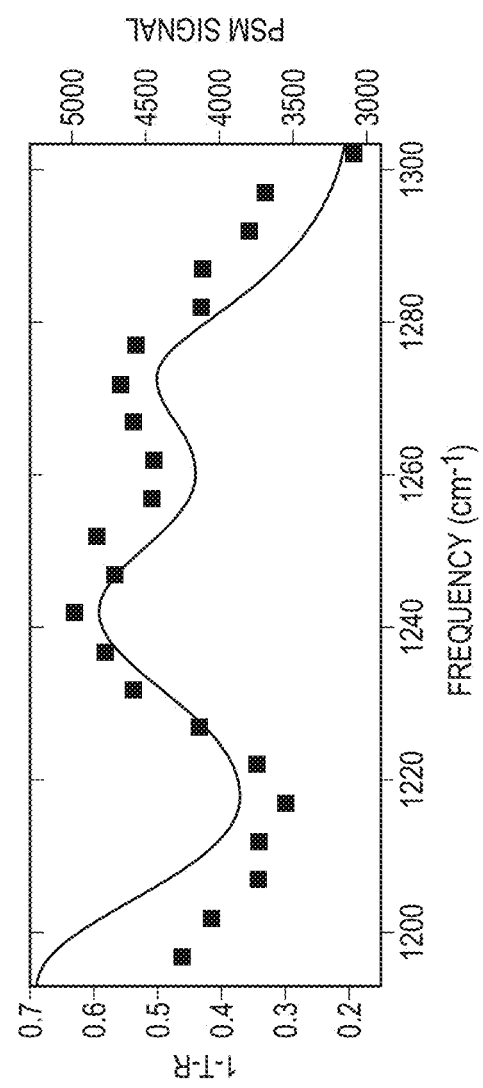
FIG. 7D is a graph illustrating a PSM spectrum of Poly(methyl methacrylate) (PMMA) microspheres on a stainless steel, absorbing substrate, the spectrum obtained using an embodiment device.

FIG. 7D is a graph illustrating a PSM spectrum (see square data points) of PMMA microspheres on a stainless steel, substrate, the PSM spectrum obtained using an embodiment device. While Ge and KBr substrates are substantially transparent at the pump laser wavelengths used for these experiments, stainless steel absorbs at these wavelengths. Also shown in FIG. 7D is a known absorption spectrum 1-T-R of stainless steel, which is similar to the measured spectrum based on PSM. FIG. 7D thus illustrates that PMMA microspheres can be distinguished using embodiments of the invention even when a substrate absorbs at the pump light wavelengths. FIGS. 7A-7D thus illustrate how an absorption spectrum of a target specimen can be determined based on the changes in positions of speckle lopes that are correlated with pump modulation. A processor or correlator such as correlator 117 in FIG. 1A can be configured to perform an FFT, for example, or other frequency analysis, thus determining correlation of the changes in positions of speckle lobes with the pump modulation frequency and rejecting from consideration in a PSM signal any changes in position that are not related to pump modulation.

Figure 8B:
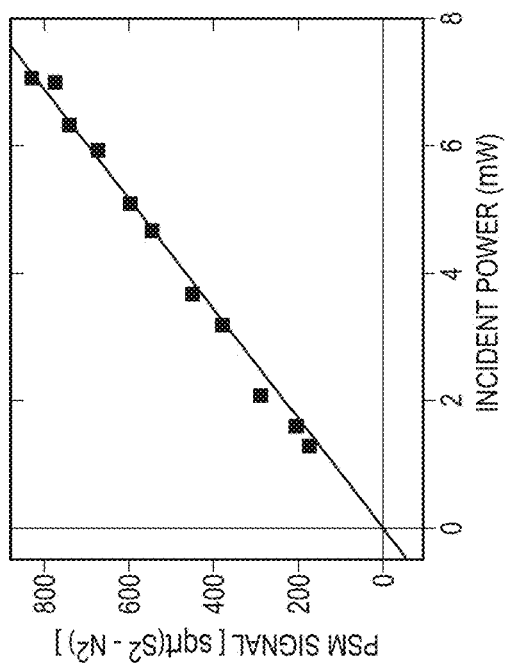
FIG. 8B is a graph illustrating that, with appropriate definition, PSM signal proportional to pump light power and can be normalized with respect to power.
Figure 8A:
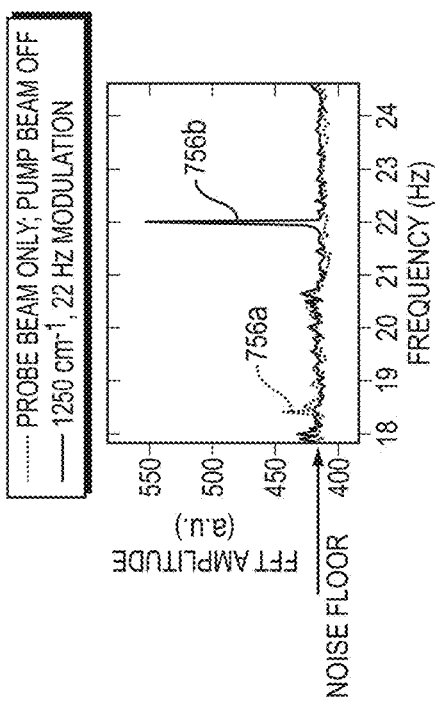
FIG. 8A is a graph illustrating how a PSM signal can be obtained with a high degree of sensitivity and noise reduction.

FIGS. 8A and 8B show graphs illustrating how a photothermal speckle modulation (PSM) signal can be obtained with a high degree of sensitivity and noise reduction and enable power normalization. In particular, where a sensor includes a pixel array, an averaged signal representing the intensity change of the speckle pattern (or motion) across all pixels can be developed as follows. The graph in FIG. 8A shows an FFT (in arbitrary units, a.u.) averaged across all FFTs for individual pixels of the pixel array as a function of frequency, as described hereinabove. Furthermore, where the PSM signal is defined appropriately, sensitivity can be further enhanced, and power normalization can be easily performed to account for any difference in pump powers at different modulation frequencies or wavelengths. This can be done as described hereinafter.

A dotted line 756a in FIG. 8A shows the averaged FFT amplitude as a function of frequency when only the probe beam is on, and the pump beam is off. Thus, the dotted line 756a is a noise floor for the FFT amplitude as a function of frequency. In contrast, the solid line 756b shows the FFT amplitude, averaged across all pixels, as a function of pump modulation frequency, with a pump light wavelength of 1250 $cm^{-1}$ and a pump modulation frequency of 22 Hz. As expected, the FFT amplitude shows a sharp peak at exactly 22 Hz, with essentially only noise in other frequency regions. Contributions from independent, uncorrelated noise sources add to the FFT signal in quadrature and can be subtracted out from the PSM signal using the equation PSM signal=$\sqrt{FFTamplitude^2 - Noisefloor^2}$. It should be noted that a PSM signal can also be defined in other ways, such as using the area under the FFT curve or simply the height of the FFT curve. However, defining the PSM curve as described using the equation PSM signal= $\sqrt{FFTamplitude^2 - Noisefloor^2}$ has the advantage that power can be normalized, as illustrated in FIG. 8B.

FIG. 8B illustrates the PSM signal, corrected using the above equation to eliminate the effect of the noise floor, as a function of incident pump light source power. In particular, the line in FIG. 8B is a fit of measured PSM signal values as a function of incident pump light power where the measured values are shown as squares. Notably, the fit of the corrected signal is linear and passes through zero, enabling normalization of the PSM signal over a broad range of powers. This normalization curve can be useful, for example, when the power output at different pump wavelengths is different, but known.

Figure 9B:
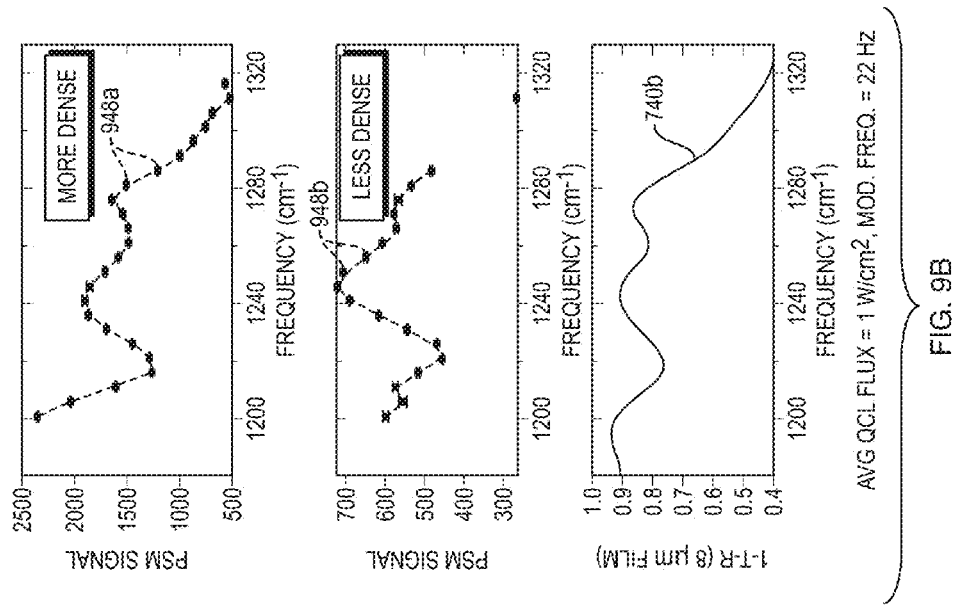
FIG. 9B is a set of graphs comparing measured PSM signals for higher and lower density clumps, respectively, of the PMMA microparticles illustrated in FIG. 9A with an absorption spectrum measured for a thin PMMA film.
Figure 9A:
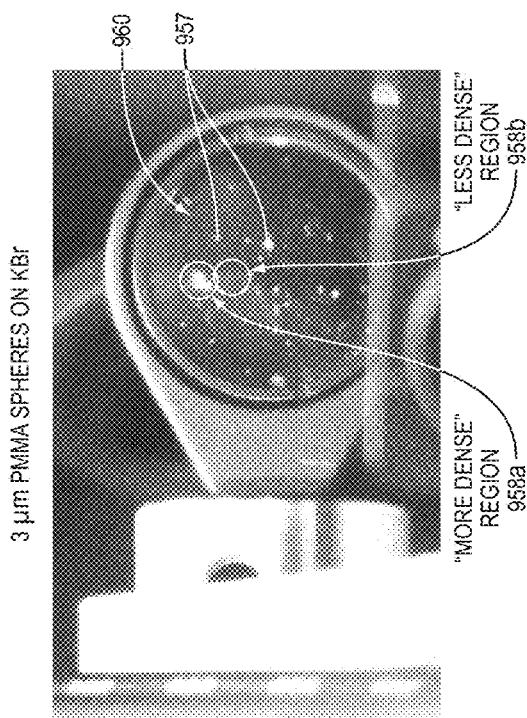
FIG. 9A is a photograph illustrating target PMMA spheres dispersed on a KBr substrate to demonstrate detection of microparticles using embodiment devices and methods.

FIGS. 9A-9B illustrate that embodiments can also detect target materials dispersed as a micropowder of micron-sized particles dispersed on a substrate, for example. FIG. 9A illustrates a sample in which PMMA spheres 957 of 3 µm diameter were dispersed on a KBr substrate 960. A relatively higher density sensing region 958a included a higher density of PMMA spheres clumped together on the substrate, while a relatively lower density sensing region 958b included less dense clumps of the PMMA spheres. FIG. 9B shows the measured PSM signal 948a for the higher density sensing region 958a, the measured PSM signals 948b for the lower density sensing region 958b, and the absorption spectrum 740b for the thin PMMA film of 8 µm thickness also illustrated in FIG. 7B. In comparing the measured PSM signals 948a and 948b with the known absorption spectrum 740b, it will be noted that the measured signals and known absorption spectrum are similar, indicating that embodiments can also be effective at distinguishing microparticles dispersed on a substrate. Advantageously, as described hereinabove, micropowders such as PMMA can still be distinguished based on absorption spectrum even when dispersed on a pump light absorbing substrate such as stainless steel. This is illustrated in FIG. 7D, for example.

FIGS. 10A and 10B are graphs illustrating differences between a frequency-based response to PSM measurements and a time-based (transient) PSM technique used for further measurements described hereinafter. All of the measurements illustrated in FIGS. 2, 5B, 5D, 5E, and 7A-7D, for example, are considered frequency-based because they rely on periodic modulation of a pump light source with one or more frequencies. Even in the measurements illustrated in FIG. 5B, for example, in which speckle modulation amplitude is obtained as a function of wavelength, each data point is acquired for each wavelength at a given modulation frequency of the pump light. In contrast to frequency-based measurements, time-based measurements need not rely on periodic modulation of pump light.

FIG. 10A is a graph showing example speckle pattern changes as a function of time. The speckle pattern is related to PSM signal as described hereinabove and starts at a time $t_0$ at which the modulated pump light source with pump modulation frequency $f_1$ is turned on. As previously described, the modulation of the pump light source can be an amplitude modulation, as illustrated in FIG. 2A, a wavelength modulation, as illustrated in FIG. 2B, or another type of modulation to which pump light absorption in the target sample can be sensitive, such as polarization modulation. The overall shape of the speckle pattern change curve illustrated in FIG. 10A is similar to the curve 334a illustrated in FIG. 3A. However, the curve in FIG. 10A includes smaller oscillations that occur a frequency $f_1$ due to pump light modulation. The smaller oscillations at frequency $f_1$ can be similar to those illustrated in the temperature curve 334b in FIG. 3B, for example, but the curve in FIG. 10A additionally shows the longer-term effects of turning on a modulated pump beam and then turning it off after many modulation periods.

In FIG. 10A, starting at time $t_0$, there is a rapid change in speckle pattern as pump light is absorbed in the target specimen and the target specimen is heated. The speckle pattern changes are also related to blurring, which is related to loss of contrast. Namely, the greater the change in positions of speckle lobes in the speckle pattern, the greater the blurring. Thus, the time scale in FIG. 10A over which speckle changes occur corresponds to the time scale over which blurring occurs. Large changes in speckle lobe positions, contrast, and blurring (e.g., during the time between $t_0$ and the region 1060a) can occur over time periods on the order of 1 second, for example. Smaller changes that occur within the region 1060a, for example, can occur over time periods related to modulation of the pump light, such as over time periods on the order of 0.1 seconds or 0.01 seconds, for example.

Over time, as the pump light modulated at frequency $f_1$ continues to illuminate the target specimen, the speckle pattern changes reach a quasi-equilibrium time 1060a, in which the speckle pattern changes reach a quasi-steady-state, with small, short-term fluctuations in the speckle pattern tracking and having correlation with the pump light source modulation. The time between $t_0$ and the region 1060a can be considered a time scale of blurring of the speckle pattern in response to thermal input. Within the region 1060a, contrast is essentially unchanged, with only small changes occurring as a result of pump beam modulation. For example, the contrast change within the region 1060a can be less than 50% of the total contrast change over the heating period between $t_0$ and the region 1060a, or less than 10% of the total contrast change, or less than 1% of the total contrast change.

The time between $t_0$ and the region 1060a can include many of the long duty cycles 330a or short duty cycles 330b illustrated in FIGS. 3A-3B, or many of the on and off modulation cycles illustrated in FIG. 1, for example. When speckle pattern changes are monitored on a time scale shorter than the time between $t_0$ and the region 1060a, for example, their correlation with the pump modulation cycles can be analyzed by a correlator such as the correlator 117 in FIG. 1A, a different processor, or by using a lock-in amplifier, for example. Furthermore, in some embodiments, speckle pattern changes can be observed or monitored by a sensor on a time scale shorter than a time scale of the pump light modulation for better correlation with the changes in speckle pattern as a function of the irradiation with the pump light source.

After a sufficient number of modulation cycles have occurred, frequency response of the target specimen can be analyzed. Such a process can be used to obtain speckle pattern change, or PSM signal at a plurality of wavelengths to obtain PSM signal as a function of wavelength, as illustrated in FIGS. 7A-7C, 7E, and 9B-9C, for example. This technique is referred to as frequency-based. Essentially, it is based on modulating a pump light source such as an IR laser beam and measuring the speckle response at that modulation frequency. Frequency-based measurements may be obtained at a plurality of pump wavelengths, as illustrated in FIG. 5B, or at a plurality of pump modulation frequencies, as illustrated in FIG. 5D, for example. When the laser is first turned on, the sample heats up and continues to heat to a steady-state average temperature. Around this average value, the temperature oscillates slightly since the laser is being modulated. This approach works well for identifying relatively optically thin materials, for example. The thickness of the thin material can be on the order of, or smaller than, the absorption depth of the pump light.

After the quasi-steady-state period 1060a, the pump light source can be turned off to allow the speckle pattern to return to its original state. Following this, the pump light can be again turned on to repeat the process at a pump modulation frequency $f_2$, and another measurement of PSM signal can be obtained within the quasi-steady state region 1060b for frequency $f_2$. Such repeated measurements of quasi-steady-state regions with different pump modulation frequencies can be used to obtain measurements such as those illustrated in FIG. 5D, for example, for thermal diffusivity-based detection of materials. Alternatively, different quasi-steady-state regions may be used to measure speckle pattern changes at a fixed frequency $f_1$, but with different respective pump laser wavelengths. In these cases, speckle modulation amplitude can be measured as a function of pump laser wavelength, as illustrated in FIG. 5B.

FIG. 10B, in contrast to FIG. 10A, illustrates transient change in speckle contrast in response to a single pump laser pulse, without pump light modulation. The speckle change curve in FIG. 10B can be similar in shape to the temperature curve 334a in FIG. 3A, for example. At time $t_0$, the pump light source is turned on. In this case, the pump light source is still turned on at time $t_0$ but there need be no further periodic modulation of pump light amplitude or pump wavelength, as illustrated in FIGS. 2A, 2B and 10A. The high-transient-change region 1061 can be analyzed for speckle pattern changes to quantify surface motion of the target specimen by observing (imaging) the speckle contrast. Thus, instead of modulating the laser, waiting for steady state, and then performing a frequency analysis, as in FIG. 10A, the time-based sensing illustrated in FIG. 10B can measure the much larger transient (non-quasi-steady state) response in the surface motion of the target to a single laser impulse. After the impulse begins, the surface of the target starts to move, and this motion causes speckle lobes in the speckle pattern resulting from reflections from the target specimen to move.

If an image of the speckle pattern is collected with an exposure time that is longer than the time it takes the speckles to move, the image will become blurry. In other words, the contrast of the image will be reduced. Measurements of speckle contrast have been used in imaging blood flow. Where blood flow is relatively greater, local speckle pattern contrast is relatively smaller, while in regions of relatively lower blood flow, speckle contrast can increase. However, in accordance with embodiments described herein, a material property of the target specimen can be determined by observing the motions or changes in intensity of the probe speckle pattern as a function of the pump light turning on or off. Furthermore, in some embodiments, changes in positions of one or more speckle lobes of the speckle pattern can be correlated with periodic pump modulation, such as the pump modulation illustrated in FIG. 1A and FIG. 2B, with the effects illustrated in FIG. 2 and FIG. 10A, for example. As illustrated in FIG. 10B, most of the blurring or change in speckle pattern occurs within a short time period 1061 after $t_0$. At the time $t_1$, the pump light source is turned off, and the speckle pattern eventually relaxes back to its original state. In FIG. 10B, there is no modulation of the pump laser light as modulation is defined herein, and particularly no periodic modulation, in contrast to the periodic modulation illustrated in FIG. 10A.

FIG. 11A is a schematic illustration of an experimental set up that can be used for time-based measurements illustrated in FIG. 10B. The pump light source 502b, which is an IR laser, and the probe light source 506, which is a green laser, are configured to irradiate the target specimen 112. The camera 111 is used to acquire an image of a speckle pattern from the target 112. A function generator 1162a triggers the camera 111 to acquire images, and a second function generator 1162b triggers the IR laser 502b to turn on. The function generators 1162a-b are synchronized such that the acquisition of images by the camera 111 and the turning on of the IR laser 502b can occur at same time.

FIG. 11B shows example timing between operation of the camera 111 and IR laser 502b used in the example setup shown in FIG. 11A. The function generator 1162a triggers the camera 111 to collect images at 20 ms exposure time for 0.5 seconds before turning on the IR laser 502b. Thus, the camera operation begins at an arbitrary initial time as shown by a camera operation curve 1164b. Operation of the IR pump laser 502b is shown in a laser operation curve 1164a. As shown in FIG. 11B, the IR laser is turned on 0.5 seconds after triggering the camera and remains on for one second before being shut off. This setup was used to obtain the measurements illustrated in FIG. 11C-11E.

FIGS. 11C-11E illustrate time-based measurements used to distinguish metal from plywood on the basis of thermal diffusivity using the apparatus described in FIGS. 11A-11B. FIGS. 11C and 11D are photographs showing a metal surface and a plywood surface, respectively, which are painted with spray paint on the surfaces to look the same to the eye. For the metal, speckle contrast measurements were performed at two spots 1166*a* and 1166*b*, and for the plywood, speckle contrast measurements were also performed for two spots 1166*c* and 1166*d*.

FIG. 11E is a graph illustrating the measured contrast as a function of time for the four spots shown in FIGS. 11C-11D for the metal and plywood, respectively. Curves 1168*a-b* show contrast as a function of time for spots 166*a-b* on the metal. Similarly, curves 168*c-d* show measured contrast as a function of time for the two spots 1166*c-d* on the plywood. As illustrated in the curves 1168*a-b*, for the metal sample in FIG. 11C, no change in contrast is observed with time when the laser is turned on or off. However, measured curves 1168*c-d* show large swings in contrast as the laser is turned on or off using the plywood target shown in FIG. 11D. Thus, FIG. 11E illustrates a clear difference in the response between the metal and plywood samples that can be used to distinguish the samples on the basis of known differences in thermal conductivities of potential target materials. FIG. 11E likewise demonstrates that the technique illustrated in FIGS. 11A-11E can even work where two target specimens have identical surfaces but have underlying materials of distinct thermal conductivities.

FIGS. 11A-11E also illustrate that, even where pump light is not modulated, changes in speckle pattern images of a probe speckle pattern can be analyzed as a function of irradiation with pump light to determine a material property such as a class of materials or a class of thermal conductivities. For example, in one embodiment method, a processor is used to track probe light speckle pattern changes as the pump light from IR laser 502*b* is turned on and then off again for a variety of different known materials in different material classes such as woods, plastics, metals, glasses, etc. For each speckle pattern, the processor calculates contrast as described above and as illustrated in FIG. 11E. Contrast data such as the curves 1168*a-b* are developed by the processor, thus calibrating the device with respect to various known target specimen materials. Afterward, the device is used to measure a contrast curve similarly for a target specimen of unknown material. The curve for the unknown target specimen has a height that is most similar to curves for one of the classes of known materials of the different material classes described above. The target specimen of (initially) unknown material is then determined to belong to the class of materials with most similar curve heights. Furthermore, if the thermal conductivities are known for the various known materials of different material classes, then the thermal diffusivity of target specimen of (initially) unknown material is then determined to be in the same range of thermal conductivities as the class of materials having contrast curves of most similar height.

Thus, even where changes in positions of speckle lobes do not have a correlation with a periodic pump modulation, embodiments such as the device of FIGS. 11A-11B, for example, can be used to determine a material property of a target or distinguish a target material of the target specimen, such as the wood or metal of FIGS. 11C-11D, from one or more additional potential target materials, by analyzing changes in images of the probe speckle pattern as a function of the irradiation with the pump light source. Speckle pattern changes can be analyzed to determine the material property using a correlator such as the correlator 117 illustrated in FIG. 1A, for example, or another processor. The correlator or processor can receive images from the camera 111 and information from the function generators 1162*a-b* about when the camera and pump laser beam 502*b* are on or off, for example. The speckle pattern changes can then be analyzed as a function of the irradiation by measuring speckle pattern change both when the pump laser beam is on and off and calculating the change in speckle pattern and contrast between on and off states.

Although contrast change of speckle images is shown in FIG. 11E instead of position or motion of speckle lobes, contrast change is related to speckle lobe position. In particular, contrast change is related to changes in the images of the probe speckle pattern that can be observed with a sensor such as the camera 111 in FIG. 11A, as further described hereinafter. The contrast change results from the photothermally induced speckle motion and reflectivity change. Speckle motion reduces the standard deviation of a speckle image (i.e. due to blurring). The change in temperature of the sample can cause the mean intensity to drop. The combined effect, in this example for the wood substrate, is an increase in contrast. Contrast is equal to the standard deviation of pixels in the image divided by mean pixel intensity in the image.

For the measurements illustrated in FIGS. 11A-11E, the on time (duty cycle) of the pump beam is 1 second, which is longer than the thermal diffusion time in the metal and plywood target samples. However, this technique can also be applied when the pump beam is on for a time (duty cycle) that is short compared to thermal diffusion time, as illustrated by the short duty cycle 330*b* and thermal profile 334*b* in FIG. 3B. In the case of short duty cycle, a sensor can be used to observe the speckle contrast change following a short-pulse excitation, and a class of materials to which the target specimen belongs can be determined based on thermal diffusivity by analyzing the contrast as a function of time following the pump excitation. Furthermore, while the measurements illustrated in FIGS. 11A-11E do not depend on periodic pump light modulation, some embodiments devices that can determine a material property of the target specimen do include pump light modulation. For example, in some embodiments, the camera and IR laser operation illustrated in FIG. 11B can be repeated periodically to obtain many contrast curves like those illustrated in FIG. 11E. Repeating the measurements periodically has the additional advantage of enabling a correlator or processor to average many curves to provide more precise determinations of a material property such as material class.

Figure 12A:
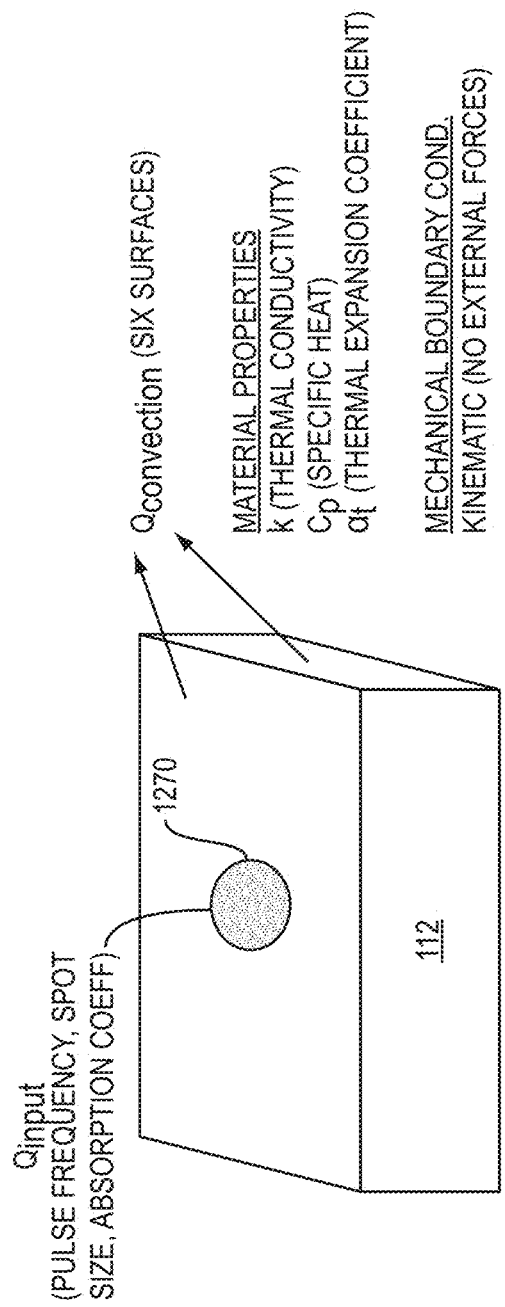
FIGS. 12A-12F illustrate assumptions and calculation results for thermo-mechanical modeling used to understand results obtained using embodiment devices and methods.

FIGS. 12A-12G illustrate thermo-mechanical modeling that can be used to understand results described hereinabove. In particular, FIG. 12A is an overview of thermal-mechanical modeling performed using a finite element analysis package referred to as Nastran®. The goal of this modeling was to determine surface motion, both radial and normal, for a given IR laser modulation frequency, target material, geometry, and boundary conditions. This thermo-mechanical model is for one experimental case of a symmetric beam. The model is helpful to show that observed behavior can be effectively modelled and explained. However, many other variations of photothermal heating are possible. For example, the pump beam need not be symmetric in any way, and there is no strict requirement on the beam properties.

As illustrated in FIG. 12A, a target specimen 112 was modelled as receiving a heat input at a spot 1270, with the heat input Q input being defined by pulse frequency, spot size, and absorption coefficient. Convection heat transfer $Q_{convection}$ was assumed to be one cooling mechanism by which the target 112 loses heat through all surfaces of the target. The material was assumed to have thermal conductivity k, specific heat $C_P$, and thermal expansion coefficient $\alpha_t$. Kinematic mechanical boundary conditions were assumed, with no external forces acting on the target 112.

Figure 12B:
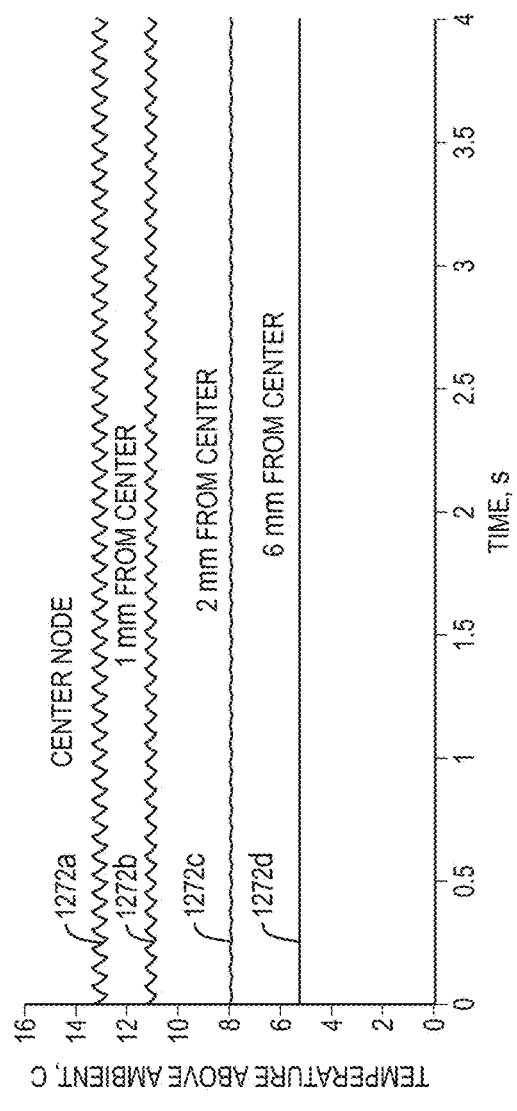
Figure 12C:
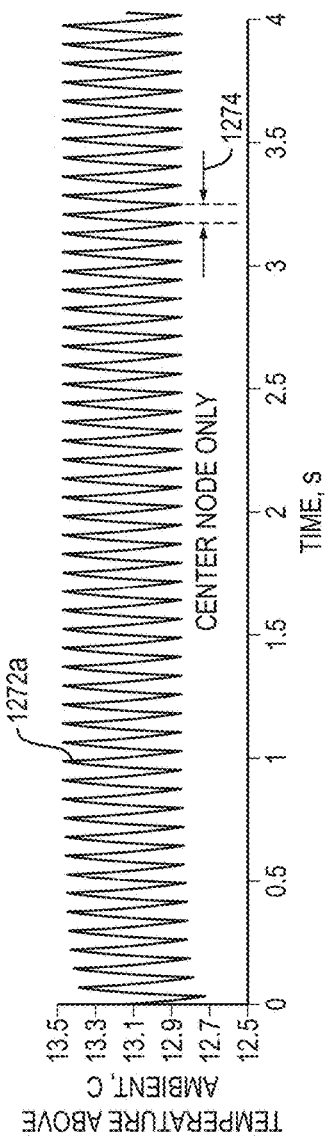

Two types of analysis can be performed using the Nastran® finite element analysis. First, a heat transfer analysis can be performed to model the temperature response to the laser-induced heat load. Second, a thermo-elastic analysis can be performed to calculate deformations of the target surface in response to the temperature changes. FIGS. 12B-12C show temperature in the target surface as a function of time and distance from the center of the spot 1270. These calculations were performed with the assumption of 10 mW average power of the laser pump source pulsed at 13 Hz modulation frequency, a 2 mm FWHM spot size, target depth D of 6.35 mm, target width W of 24 mm, Teflon material properties, and a convection coefficient of 1.4 W/(m-° C.).

FIG. 12B shows curves 1272*a-d* showing calculated temperatures as a function of time at the center of spot 1250, 1 mm from the center, 2 mm from the center, and 6 mm from the center, respectively. FIG. 12C shows the center node temperature 1272*a* in greater detail. From curve 1272*a*, it can be seen that the average temperature is 13.2° C. above ambient, while oscillations in temperature are between about 12.9° C. and about 13.5° C. during a given cycle time 1274. Furthermore, from FIG. 12B, it can be seen that as the distance from the center of the spot 1270 increases, both the average temperature and the magnitude of the oscillations dropped.

Furthermore, in addition to detecting particles, liquids, and solids, embodiment methods and devices can also be used to detect a gas remotely. The absorption of the gas leads to a speckle pattern change that can be measured in a similar manner as described for the other materials. For example, a PSM sensor can be configured to allow for standoff spectroscopic measurements of vapors. This can be achieved in the following way, under the assumption that the volumetric concentration of the gas remains fairly constant over the course of the measurement time. A target can be positioned in the distance that has a known PSM spectrum (for example, intensity versus wavelength spectrum such as that shown in FIG. 7 for a number of materials). A gas cell of known concentration can be positioned between the pump beam and the target. The pump laser can be amplitude modulated for a number of wavelengths, and PSM spectrum from the probe beam can be analyzed as described previously for each pump wavelength. At pump wavelengths that are absorbed by the gas sample, less pump light will reach the target, leading to a reduction in the PSM spectrum compared with no gas in the beam path. However, at wavelengths where the gas is transparent, the PSM signal from the target will be nearly the same with or without the presence of the gas. Therefore, by taking the ratio of the PSM spectrum with and without the gas present in the pump beam path, the absorption spectrum of the gas can be determined.

Figure 12D:
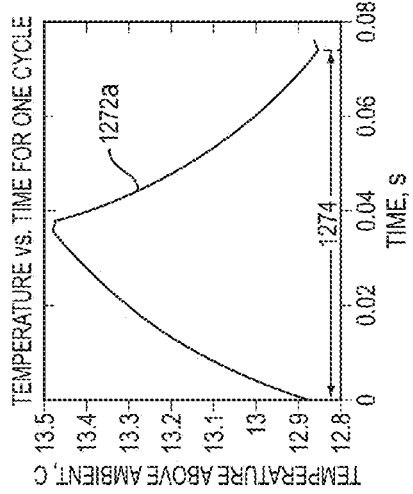

FIG. 12D illustrates the center node temperature curve 1272*a* over the single cycle region 1274 illustrated in FIG. 12C.

Figure 12F:
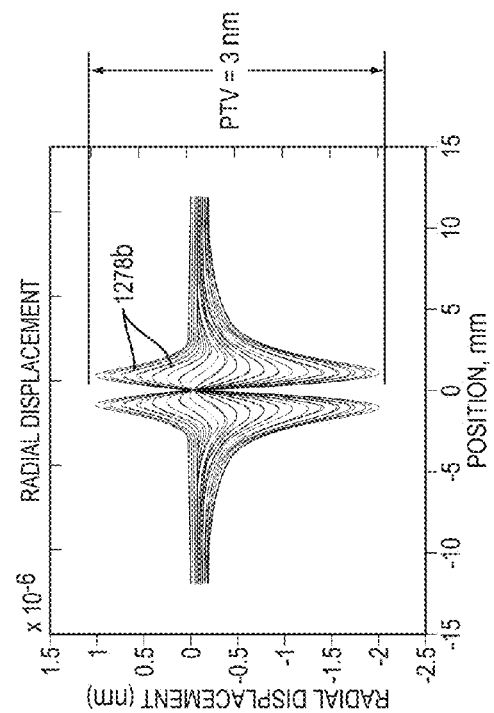
Figure 12E:
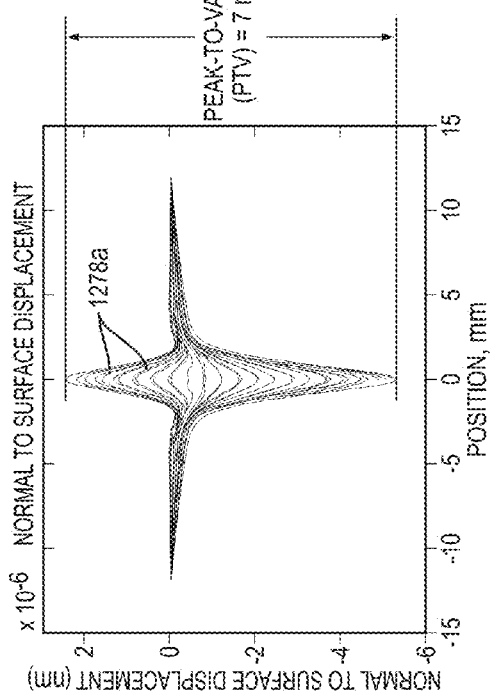

The various curves in FIGS. 12E-12F are positions along a cross section cutting through the center of the pump beam along the surface of the material.

FIG. 12E is a graph illustrating PTV normal-to-surface displacement curves 1278*a* as a function of radial position from the center of the spot 1270 at various times. The various curves 1278*a* in FIG. 12E represent different times, and each curve shows displacement in a plane that intersects the center of the pump beam and is perpendicular to the target surface, at various points along the target surface. FIG. 12E shows that the displacement normal to the surface the largest amplitude (7 nm) at the center of the spot 1270 (position 0 mm). It can also be seen that the PTV displacements are in the range of a few nanometers.

FIG. 12F is a graph illustrating radial displacements 1278*b* as a function of position (distance from the center of the spot 1270) at various times. Each curve represents a different time. As seen in FIG. 12F, the maximum PTV radial displacement is about 3 nm.

Since material properties such as spectral absorption and thermal diffusivity directly affect changes in positions of speckle lobes in a speckle pattern of a target specimen, therefore, the modeling illustrated in FIGS. 12A-12F can be used to understand relative magnitudes of the changes in positions that should be expected for different materials. Thus, the thermo-mechanical modeling illustrated in FIGS. 12A-12F can be used to predict relative speckle deflections and help determine material properties such as absorption spectra, chemical species, or material classes based on such deflections.

While this invention has been particularly shown and described with references to example embodiments thereof, it will be understood by those skilled in the art that various changes in form and details may be made therein without departing from the scope of the invention encompassed by the appended claims.

What is claimed is:

1. A device comprising:
   a pump light source configured to be modulated over a range of pump modulation frequencies and to irradiate a target specimen;
   a probe light source arranged to generate a speckle pattern from the target specimen; and
   a sensor configured to detect changes in at least one of position and intensity of one or more speckle lobes of the speckle pattern having correlation with the pump modulation over the range of pump modulation frequencies.

2. The device of claim 1, wherein the pump modulation is on a time scale shorter than a time scale of blurring of the speckle pattern, and wherein the sensor is configured to detect the changes in at least one of position and intensity on a time scale shorter than the time scale of blurring the speckle pattern.

3. The device of claim 1, further comprising a correlator configured to perform a frequency analysis to determine correlation of the changes in at least one of position and intensity of the one or more speckle lobes with frequency of the pump modulation over the range of pump modulation frequencies.

4. The device of claim 1, further comprising a processor configured to determine an absorption spectrum of the target specimen based on the changes in positions of the one or more speckle lobes.

5. The device of claim 1, further comprising a processor configured to identify a material class of the target specimen based on the changes in at least one of position and intensity of the one more speckle lobes.

6. The device of claim 5, wherein the processor is further configured to identify the material class independent of a surface material of the target specimen.

7. The device of claim 1, further comprising a processor configured to determine a thermal diffusivity of the target specimen based on the changes in at least one of position and intensity of the one or more speckle lobes.

8. The device of claim 1, wherein at least one duty cycle of the pump modulation is short in comparison with a thermal diffusion time of the target specimen.

9. The device of claim 1, wherein the pump modulation is a light amplitude modulation.

10. The device of claim 1, wherein the pump modulation is a wavelength modulation or a light polarization modulation.

11. The device of claim 1, wherein the pump light source is further configured to irradiate the target specimen with a plurality of wavelengths of pump light simultaneously.

12. The device of claim 11, wherein the pump light source is configured to irradiate the target specimen with the plurality of wavelengths at different locations of the target specimen.

13. The device of claim 11, wherein the pump light source is further configured to modulate light amplitude of the plurality of wavelengths at respective, mutually distinct light amplitude modulation frequencies and to irradiate the target specimen with the plurality of wavelengths at least partially overlapping at the target specimen.

14. The device of claim 1, wherein the pump light source is configured to irradiate the target specimen with pump light of a fixed wavelength and the pump modulation is light amplitude modulation, the pump light source being further configured to output the light at a plurality of amplitude modulation frequencies, and wherein the sensor is configured to detect changes in at least one of position and intensity of the one or more speckle lobes having correlation with the plurality of frequencies of the light amplitude modulation.

15. The device of claim 1, wherein the probe light source is further configured to generate a speckle pattern from a given region of the target specimen, and wherein the sensor is further configured to detect changes in at least one of position and intensity of the one or more speckle lobes at different positions in the given region of the target specimen.

16. The device of claim 1, wherein the probe light source is further configured to generate the speckle pattern from a position inside the target specimen, the probe light passing through an outer surface of the target specimen to the position inside the target specimen.

17. The device of claim 1, wherein the sensor comprises an array of detector elements comprising photomultiplier tubes (PMTs), CCD array elements, CMOS array elements, photodiode array elements, or photosensitive fibers.

18. A method comprising:
modulating a pump light source over a range of pump modulation frequencies;
irradiating a target specimen with light from the pump light source;
generating a probe light speckle pattern from the target specimen; and
detecting changes in at least one of position and intensity of one or more speckle lobes of the speckle pattern having correlation with the pump modulation over the range of pump modulation frequencies.

19. The method of claim 18, modulating at the pump modulation includes modulating on a time scale shorter than a time scale of blurring of the speckle pattern, and wherein detecting the changes in at least one of position and intensity includes detecting on a time scale shorter than the time scale of blurring of the speckle pattern.

20. The method of claim 18, further comprising performing a frequency analysis to determine correlation of the changes in at least one of position and intensity of the one or more speckle lobes with frequency of the pump modulation over the range of pump modulation frequencies.

21. The method of claim 18, further comprising determining an absorption spectrum of the target specimen based on the changes in at least one of position and intensity of the one or more speckle lobes.

22. The method of claim 18, further comprising determining a thermal diffusivity of the target specimen based on the changes in positions of the one or more speckle lobes.

23. The method of claim 18, further comprising distinguishing between potential classes of materials of the target specimen based on the changes in at least one of position and intensity of the one or more speckle lobes.

24. The method of claim 23, wherein distinguishing between potential classes of materials is done independently of an optical property of a surface of the target specimen.

25. The method of claim 18, wherein modulating the pump light source includes modulating with at least one duty cycle that is short in comparison with a thermal diffusion time of the target specimen.

26. The method of claim 18, wherein modulating the pump light source includes modulating a light amplitude.

27. The method of claim 18, wherein modulating the pump light source includes modulating wavelength or modulating light polarization.

28. The method of claim 18, wherein irradiating the target specimen with light from the pump light source includes irradiating with a plurality of wavelengths of pump light simultaneously.

29. The method of claim 28, wherein irradiating with the plurality of wavelengths of pump light includes irradiating with the plurality of wavelengths at different locations of the target specimen.

30. The method of claim 28, wherein irradiating with the plurality of wavelengths includes irradiating with the plurality of wavelengths at least partially overlapping at the target specimen, the method further comprising modulating light amplitudes of the plurality of wavelengths at mutually distinct light amplitude modulation frequencies, the method further comprising performing a frequency analysis to determine correlation of the changes in at least one of position and intensity of the one or more speckle lobes with respect to the respective wavelengths.

31. The method of claim 18, wherein modulating the pump light source includes modulating light amplitude, wherein irradiating with light from the pump light source includes irradiating with pump light of a fixed wavelength, irradiating further including outputting the light from the pump light source at a plurality of amplitude modulation frequencies, and wherein detecting the changes in at least one of position and intensity of the one or more speckle lobes includes detecting the changes having correlation with the plurality of frequencies of the light amplitude modulation.

32. The method of claim 18, wherein detecting the changes in at least one of position and intensity of the one or more speckle lobes includes detecting changes in at least one of position and intensity of speckle lobes at different positions at the target specimen.

33. The method of claim 18, wherein generating the probe speckle pattern from the target specimen includes generating the pattern at a position inside the target specimen, the probe light passing through an outer surface of the target specimen to the position inside the target specimen.

34. The method of claim 18, wherein detecting includes using an array of detector elements.

35. The method of claim 34, wherein using the array of detector elements includes using photomultiplier tubes (PMTS), CCD array elements, CMOS array elements, photodiode array elements, or photosensitive fibers.

36. The method of claim 18, wherein modulating the pump light source includes using an infrared laser.

37. A device comprising:
   means for modulating pump light source over a range of pump modulation frequencies;
   means for irradiating a target specimen with light from the pump light source;
   means for generating a probe light speckle pattern from the target specimen; and
   means for detecting changes in at least one of position and intensity of one or more speckle lobes of the speckle pattern having correlation with the pump modulation over the range of pump modulation frequencies.

* * * * *